(12) United States Patent
Horiuchi et al.

(10) Patent No.: US 11,643,430 B2
(45) Date of Patent: May 9, 2023

(54) PORPHYRIN COMPOUND OR SALT THEREOF, CANCER THERAPEUTIC AGENT, PHOTOSENSITIZER, AND FLUORESCENT PROBE

(71) Applicants: M.T.3, Inc., Tokyo (JP); NATIONAL UNIVERSITY CORPORATION GUNMA UNIVERSITY, Maebashi (JP)

(72) Inventors: Hiroaki Horiuchi, Kiryu (JP); Masahiko Oshige, Isesaki (JP); Ichiro Matsuo, Kiryu (JP); Tetsuo Okutsu, Maebashi (JP); Shinji Katsura, Kiryu (JP); Toshitada Yoshihara, Midori (JP); Seiji Tobita, Maebashi (JP); Fumio Sugawara, Tokyo (JP); Kengo Sakaguchi, Tsukuba (JP)

(73) Assignees: M.T.3, INC., Tokyo (JP); NATIONAL UNIVERSITY CORPORATION GUNMA UNIVERSITY, Maebashi (JP)

( * ) Notice: Subject to any disclaimer, the term of this patent is extended or adjusted under 35 U.S.C. 154(b) by 107 days.

(21) Appl. No.: 17/462,279

(22) Filed: Aug. 31, 2021

(65) Prior Publication Data
US 2022/0064203 A1    Mar. 3, 2022

(30) Foreign Application Priority Data
Sep. 1, 2020    (JP) .............................. JP2020-146971

(51) Int. Cl.
*C07H 17/02*    (2006.01)
*A61K 41/00*    (2020.01)

(52) U.S. Cl.
CPC ......... *C07H 17/02* (2013.01); *A61K 41/0071* (2013.01)

(58) Field of Classification Search
CPC .... C07H 17/02; C07H 23/00; A61K 41/0071; A61N 5/062; A61P 35/00; C09B 47/00
See application file for complete search history.

(56) References Cited

U.S. PATENT DOCUMENTS

| | | | |
|---|---|---|---|
| 4,935,498 A | 6/1990 | Sessler et al. | |
| 6,630,128 B1 | 10/2003 | Love et al. | |
| 2004/0259810 A1* | 12/2004 | Grierson | A61P 35/00 514/23 |

FOREIGN PATENT DOCUMENTS

| | | | |
|---|---|---|---|
| JP | 2002523509 A | 7/2002 | |
| JP | 2004002438 A | 1/2004 | |
| JP | 5843113 B2 | 11/2015 | |
| WO | 2012029609 A1 | 3/2012 | |

OTHER PUBLICATIONS

Horiuchi, Hiroaki, et al., "Silylation enhancement of photodynamic activity of tetraphenylporphyrin derivative", J. Photochem. Photobiol. A, 2011, 221, pp. 98-104.
Horiuchi, Hiroaki, "Silylation Improves the Photodynamic Activity of Tetraphenylporphyrin Derivatives In Vitro and In Vivo", Chem. Eur. J., 2014, vol. 20, pp. 6054-6060.
Horiuchi, Hiroaki, et al., "The effect of central metal on the photodynamic properties of silylated tetraphenylporphyrin derivative", J. Photochem. Photobiol. A, 2016, 321, pp. 72-78.
Kataoka, Hiromi, et al., "Development of Novel Photodynamic Therapy and Diagnosis by using Sugar Chain Conjugated Chlorine", JJSLSM, vol. 34, vol. 2, 2013, pp. 113-117.
Kato, Harubumi, "Our Experience With Photodynamic Diagnosis and Photodynamic Therapy for Lung Cancer", Journal of the National Comprehensive Cancer Network, 10 (2012), S-3 to S-8. (6 pages).
Lang, K., et al., "Photophysical properties of porphyrinoid sensitizers non-covalently bound to host molecules; models for photodynamic therapy", Coordination Chemistry Reviews, 248 (2004), pp. 321-350.

* cited by examiner

*Primary Examiner* — Jonathan S Lau
(74) *Attorney, Agent, or Firm* — Buchanan, Ingersoll & Rooney PC

(57) ABSTRACT

There is provided with a porphyrin compound represented by Formula (I) or a salt thereof;

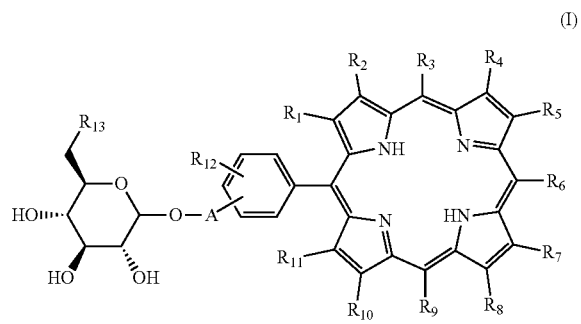

where A is a linking group represented as —X—NHCO— where X is a $C_1$ to $C_6$ alkylene group, each of $R_1$, $R_2$, $R_4$, $R_5$, $R_7$, $R_8$, $R_{10}$, and $R_{11}$ is a hydrogen atom, each of $R_3$, $R_6$, and $R_9$ is a substituent of Formula; $R_{12}$ is selected from a group of substituents represented by Formulae, $R_{13}$ is a sulfo group, Ra, Rb, and Rc are substituents independently selected from $C_1$ to $C_6$ alkyl groups, and Rd is a hydrogen atom or a $C_1$ to $C_6$ alkyl group, and Rx is a substituent represented by General Formula. The porphyrin compound is useful as a cancer therapeutic agent, photosensitizer and fluorescent probe.

9 Claims, 33 Drawing Sheets

PORPHYRIN COMPOUND OR SALT THEREOF, CANCER THERAPEUTIC AGENT, PHOTOSENSITIZER, AND FLUORESCENT PROBE

CROSS-REFERENCE TO RELATED APPLICATION(S)

This application claims priority to and the benefit of Japanese Patent Application No. 2020-146971 filed on Sep. 1, 2020, the entire disclosure of which is incorporated herein by reference.

BACKGROUND OF THE INVENTION

Field of the Invention

The present invention relates to a compound or a salt thereof, and a method.

Description of the Related Art

A technique (photodynamic therapy) is known in which a compound that can generate singlet oxygen (photosensitizing agent) is administered to a patient with cancer or the like and then is irradiated with light of an appropriate wavelength to generate singlet oxygen, and thereby malignant cells are disrupted and the disease is treated. Moreover, many photosensitizing agents also emit fluorescence, and photodynamic diagnosis is also known in which such agents are irradiated with light of an appropriate wavelength and fluorescence emitted therefrom is observed to diagnose cancers and the like. As such a treatment/diagnosis technique, techniques have been developed in which compounds obtained by adding a silicon-containing substituent to porphyrin analogs, phthalocyanine derivatives, hypocrellin derivatives, hypericin derivatives, and the like, which have been used in conventional techniques (see Japanese Patent Laid-Open No. 2002-523509, Japanese Patent Laid-Open No. 2004-002438, K. Lang et al., "Photophysical properties of porphyrinoid sensitizers non-covalently bound to host molecules; models for photodynamic therapy" Coordination Chemistry Reviews, 248 (2004), p 321-35, and Harubumi Kato, "Our Experience With Photodynamic Diagnosis and Photodynamic Therapy for Lung Cancer", Journal of the National Comprehensive Cancer Network, 10 (2012), S-3-8, for example) are used, and the usefulness thereof has been revealed (International Publication No 2012/029609, Japanese Patent No. 5843113, Hiroaki Horiuchi et al., "Silylation enhancement of photodynamic activity of tetraphenylporphyrin derivative", J. Photochem. Photobiol. A, 2011, 221, 98-104, Hiroaki Horiuchi, "Silylation Improves the Photodynamic Activity of Tetraphenylporphyrin Derivatives In Vitro and In Vivo", Chem. Eur. J., 2014, 20, 6054-6060, and Hiroaki Horiuchi, "The effect of central metal on the photodynamic properties of silylated tetraphenylporphyrin derivative", J. Photochem. Photobiol. A, 2016, 321, 72-8). On the other hand, sugar chain-linked chlorin that enables high tumor-cell tropism has been developed by linking glucose to a photosensitive fluorescent substance chlorin, and it has been revealed that it has tumor selectivity (Hiromi Kataoka et al, "Development of Novel Photodynamic Therapy and Diagnosis by using Sugar Chain Conjugated Chlorine", JJSLSM, 34 (2013), 113-7).

SUMMARY OF THE INVENTION

According to one embodiment of the present invention, a compound is represented by Formula (I) below or a salt thereof;

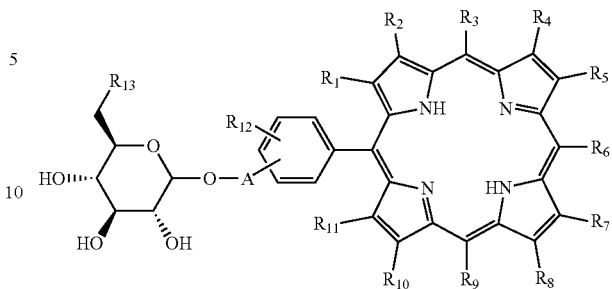

where A is a linking group represented as —X—NHCO— where X is a $C_1$ to $C_6$ alkylene group, $R_1$, $R_2$, $R_4$, $R_5$, $R_7$, $R_8$, $R_{10}$, and $R_{11}$ each are a hydrogen atom, $R_3$, $R_6$, and $R_9$ each are a substituent of Formulae (iii) below;

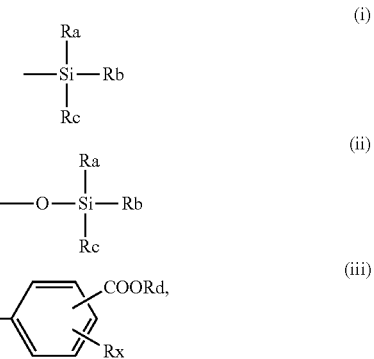

$R_{12}$ is selected from substituents represented by Formulae (i) and (ii) above, $R_{13}$ is a sulfo group, Ra, Rb, and Rc in Formulae (i) and (ii) above are independently a substituent selected from $C_1$ to $C_6$ alkyl groups, and Rd in Formula (iii) above is a hydrogen atom or a $C_1$ to $C_6$ alkyl group, and Rx in Formula (iii) above is a substituent represented by General Formula (i) or (ii) above.

According to another embodiment of the present invention, a method of treating a patient suffering from cancer, comprises administering, to the patient, an effective amount of a compound or the salt thereof, wherein the compound is represented by Formula (I) below or a salt thereof;

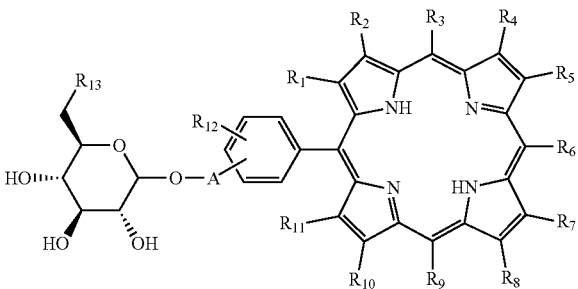

where A is a linking group represented as —X—NHCO— where X is a C$_1$ to C$_6$ alkylene group, each of R$_1$, R$_2$, R$_4$, R$_5$, R$_7$, R$_8$, R$_{10}$, and R$_{11}$ is a hydrogen atom, each of R$_3$, R$_6$, and R$_9$ is a substituent of Formulae (iii) below;

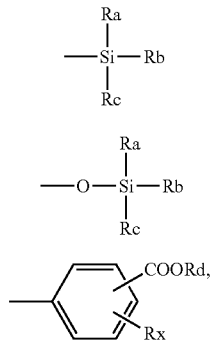

(i)

(ii)

(iii)

R$_{12}$ is selected from a group of substituents represented by Formula (i) or (ii) above, R$_{13}$ is a sulfo group, Ra, Rb, and Rc in Formula (i) and (ii) above are substituents independently selected from C$_1$ to C$_6$ alkyl groups, and Rd in Formula (iii) above is a hydrogen atom or a C$_1$ to C$_6$ alkyl group, and Rx in Formula (iii) above is a substituent represented by General Formula (i) or (ii) above.

According to yet another embodiment of the present invention, a method comprises administering a photosensitizing agent for photodynamic therapy containing a compound or the salt thereof, wherein the compound is represented by Formula I below or a salt thereof;

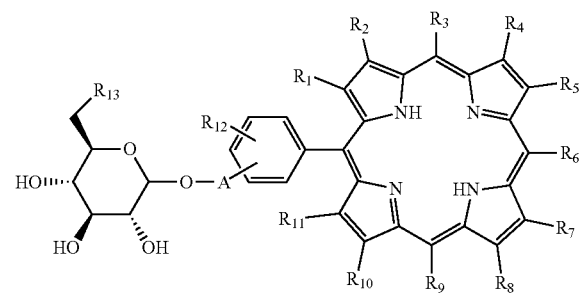

(I)

where A is a linking group represented as —X—NHCO— where X is a C$_1$ to C$_6$ alkylene group, each of R$_1$, R$_2$, R$_4$, R$_5$, R$_7$, R$_8$, R$_{10}$, and R$_{11}$ is a hydrogen atom, each of R$_3$, R$_6$, and R$_9$ is a substituent of Formulae (iii) below;

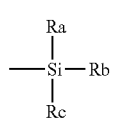

(i)

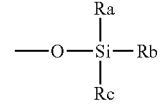

(ii)

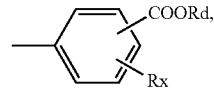

(iii)

R$_{12}$ is selected from a group of substituents represented by Formula (i) or (ii) above, R$_{13}$ is a sulfo group, Ra, Rb, and Rc in Formula (i) and (ii) above are substituents independently selected from C$_1$ to C$_6$ alkyl groups, and Rd in Formula (iii) above is a hydrogen atom or a C$_1$ to C$_6$ alkyl group, and Rx in Formula (iii) above is a substituent represented by General Formula (i) or (ii) above.

According to still another embodiment of the present invention, a method comprises administering a fluorescent probe composition containing a compound or the salt thereof, wherein the compound is represented by Formula (I) below or a salt thereof;

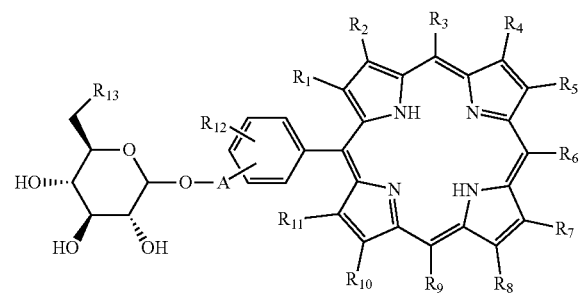

(I)

where A is a linking group represented as —X—NHCO— where X is a C$_1$ to C$_6$ alkylene group, each of R$_1$, R$_2$, R$_4$, R$_5$, R$_7$, R$_8$, R$_{10}$, and R$_{11}$ is a hydrogen atom, each of R$_3$, R$_6$, and R$_9$ is a substituent of Formulae (iii) below;

DESCRIPTION OF THE EMBODIMENTS

Figure 1:
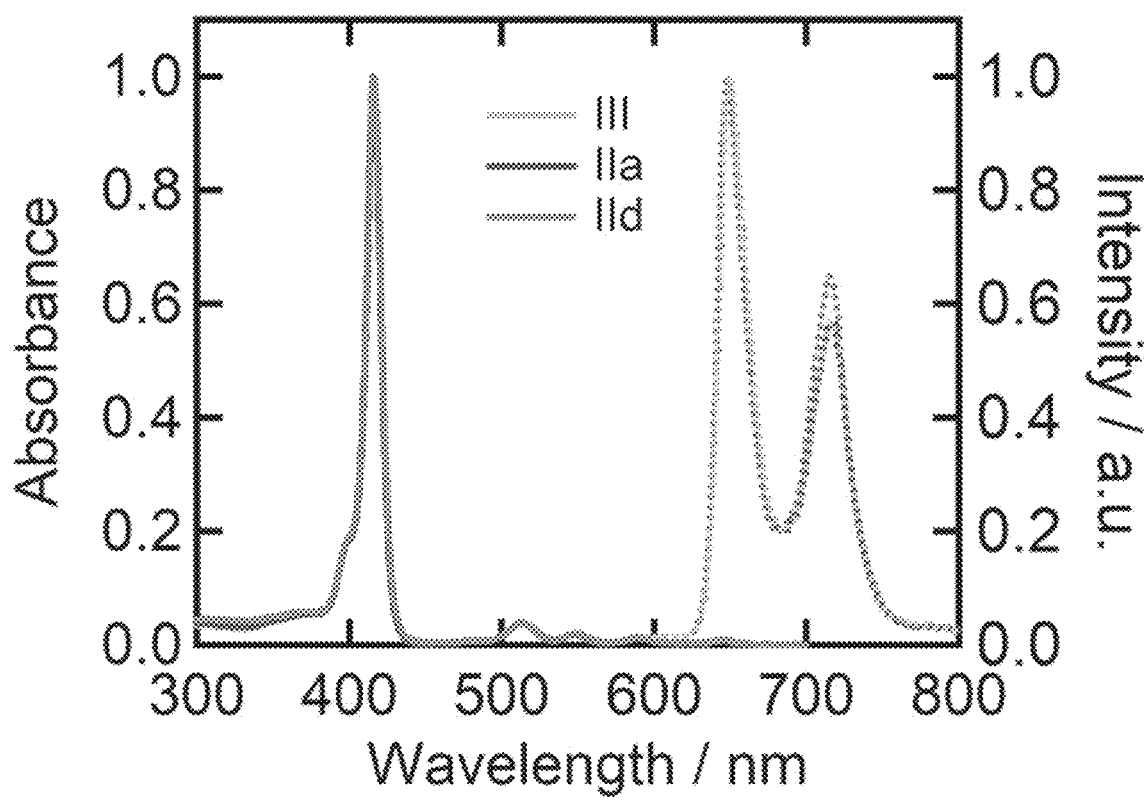
FIG. 1 shows absorption spectra and fluorescence spectra of compounds according to Example 3.

Hereinafter, embodiments will be described in detail with reference to the attached drawings. Note, the following embodiments are not intended to limit the scope of the claimed invention, and limitation is not made to an invention that requires a combination of all features described in the embodiments. Two or more of the multiple features described in the embodiments may be combined as appropriate. Furthermore, the same reference numerals are given to the same or similar configurations, and redundant description thereof is omitted.

A compound according to one embodiment of the present invention is represented by General Formula (I) below.

[Chemical Formula 3]

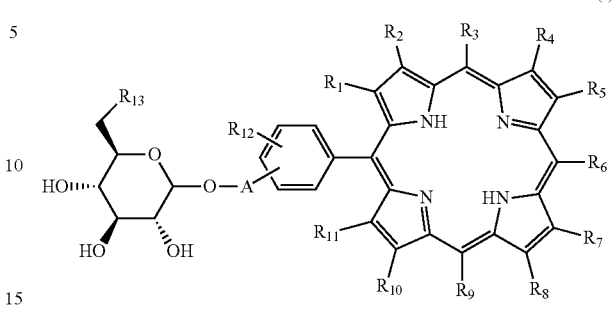

(I)

In General Formula (I), A is a divalent linking group. There is no particular limitation on the type of divalent linking group, and examples thereof include divalent aliphatic hydrocarbon groups, divalent heterocyclic groups, an amino group (—NH—), and a carbonyl group, and linking groups in which an ether group (—O—), a hydroxy group, or the like is further linked to the above-mentioned linking groups.

In this specification, a hydrocarbon group may be an aliphatic hydrocarbon group or an aromatic hydrocarbon group. Examples of the aliphatic hydrocarbon group include alkyl groups such as a methyl group, an ethyl group, a hexyl group, and cyclohexyl group; alkenyl groups such as an ethenyl group and a hexenyl group; and alkynyl groups such as an ethynyl group and a hexynyl group. Examples of the aromatic hydrocarbon group include a phenyl group and a naphthyl group. A heterocyclic group may be an aromatic heterocyclic group or an aliphatic heterocyclic group. Examples of the aromatic heterocyclic group include a thienyl group and a pyridyl group. Examples of the aliphatic heterocyclic group include a tetrahydrofuranyl group and a pyrrolidinyl group. It should be noted that the divalent aliphatic hydrocarbon group and the divalent aromatic group respectively correspond to groups obtained by removing one hydrogen atom from an aliphatic hydrocarbon group and an aromatic group as mentioned above.

In one embodiment, A is represented as —X—Y—, where X links to the oxygen atom and Y links to the benzene ring together with $R_{12}$. Here, X is a $C_1$ to $C_{20}$ divalent hydrocarbon group, for example. In one embodiment, X is a $C_1$ to $C_6$ divalent hydrocarbon group, and, for example, X is a $C_1$ to $C_6$ alkylene group. Specific examples of X include linear alkylene groups such as a methylene group, an ethylene group, a propane-1,3-diyl group, butane-1,4-diyl group, and a hexane-1,6-diyl group; and branched alkylene groups such as propane-1,2-diyl group and 2-methylpentane-1,5-diyl group. Y is an amide group. In one embodiment, the C=O moiety included in the amide group links to the benzene ring together with $R_{12}$, and the nitrogen atom included in the amide group links to X. The amide group can be represented as —NR$_Y$CO—, where R$_Y$ may be a hydrogen atom or a $C_1$ to $C_6$ hydrocarbon group.

In Formula (I), $R_1$ to Rn are monovalent substituents. For example, $R_1$ to $R_{11}$ may be independently a hydrogen atom, a methylene group, a carboxyl group (e.g., —CH$_2$COOH, —CH$_2$CH$_2$COOH, or —CH$_2$COCH$_2$CH(CH$_2$COOH)COOH), a hydroxy group, a sulfo group (—SO$_3$H), or a hydrocarbon group (CH$_3$ or CH$_2$CH$_3$).

On the other hand, at least one of $R_1$ to Rn is selected from substituents represented by General Formulae (i) to (iii) below.

[Chemical Formula 4]

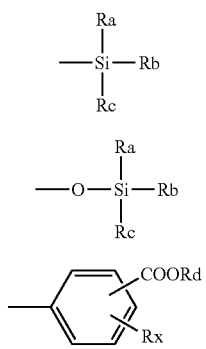

In General Formulae (i) and (ii), Ra, Rb, and Rc are independently a substituent selected from a hydrogen atom, $C_1$ to $C_6$ aliphatic hydrocarbon groups, $C_1$ to $C_6$ alkoxy groups, and $C_2$ to $C_{10}$ aromatic groups. Examples of the alkoxy groups include a methoxy group, an ethoxy group, a propoxy group, a t-butoxy group, a phenoxy group, a pentyloxy group, an allyloxy group, and a cyclohexyloxy group.

In General Formula (iii), Rd is a substituent selected from a hydrogen atom and $C_1$ to $C_6$ aliphatic hydrocarbon groups, and Rx is a substituent represented by General Formula (i) or (ii). There is no particular limitation on the positions on the phenyl ring to which COORd and Rx link in General Formula (iii). On the other hand, in one embodiment, the substituents COORd and Rx link to meta positions relative to the porphyrin ring-linking site.

Here, it is more preferable that at least one of $R_1$ to $R_{11}$ is a substituent represented by (iii) that has Rx represented by (i). Moreover, in one embodiment, $R_3$, $R_6$, and $R_9$ are selected from substituents represented by Formulae (i) to (iii) above. For example, in one embodiment, $R_3$, $R_6$, and $R_9$ are substituents represented by Formula (iii) above, and, in this case, Rx may be a substituent represented by Formula (i). Moreover, in this case, Rd may be a hydrogen atom or a $C_1$ to $C_6$ aliphatic hydrocarbon group. Moreover, in this case, Ra, Rb, and Rc may be independently a $C_1$ to $C_6$ aliphatic hydrocarbon group. Furthermore, in this case, $R_1$, $R_2$, $R_4$, $R_5$, $R_7$, $R_8$, $R_{10}$, and $R_{11}$ may be hydrogen atoms.

In Formula (I), $R_{12}$ is selected from substituents represented by Formulae (i) and (ii) above. Here, Ra, Rb, and Rc may be trialkylsilyl groups such as a trimethylsilyl group, or trialkylsiloxy groups such as a trimethylsiloxy group.

It should be noted that there is no particular limitation on the positions on the phenyl group to which A and $R_{12}$ link. On the other hand, in one embodiment, the substituents A and $R_{12}$ link to meta positions relative to the porphyrin ring-linking site.

In Formula (I), $R_{13}$ is a hydroxy group or a sulfo group. A sulfo group can be employed as $R_{13}$ from the viewpoint of improving the efficiency of uptake of the compound represented by Formula (I) by tumor cells.

A compound according to another embodiment of the present invention is a compound represented by Formula (IIb) below. The compound represented by Formula (IIb) below is an example of the compounds represented by General Formula (I).

[Chemical Formula 5]

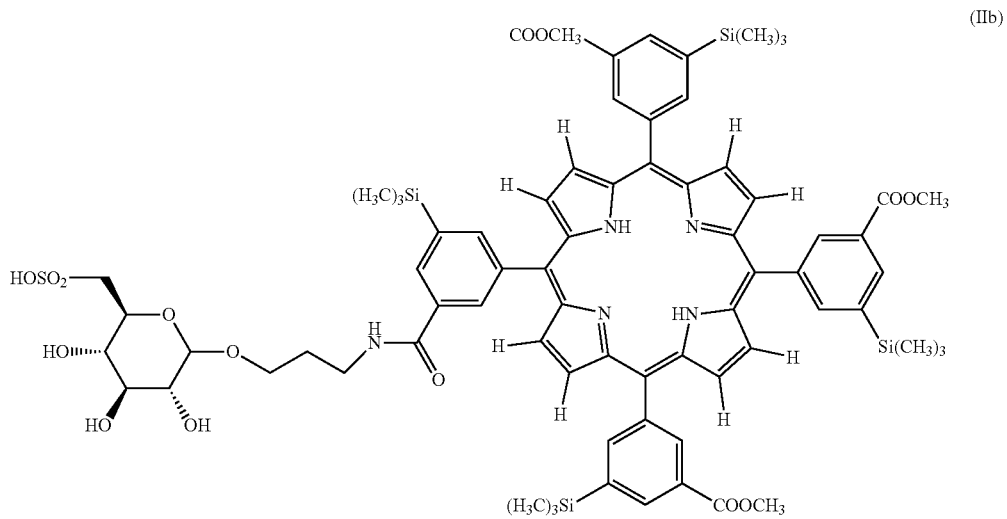

A compound according to yet another embodiment of the present invention is a salt of a compound represented by General Formula (I) above. A sodium salt, a potassium salt, or the like may be used as the salt. For example, $R_{13}$ in Formula (I) may be a salt of a sulfo group. Moreover, in a compound of General Formula (I), a metal such as $Zn^{2+}$, $Cu^{2+}$ (II), $Ca^{2+}$, $Mg^{2+}$, or $SiR_2$ may link to the center of the porphyrin ring to form a salt.

Examples of a compound according to one embodiment of the present invention include compounds (IIa) and (IIc) below, which are salts of the compound represented by Formula (IIb).

[Chemical Formula 6]

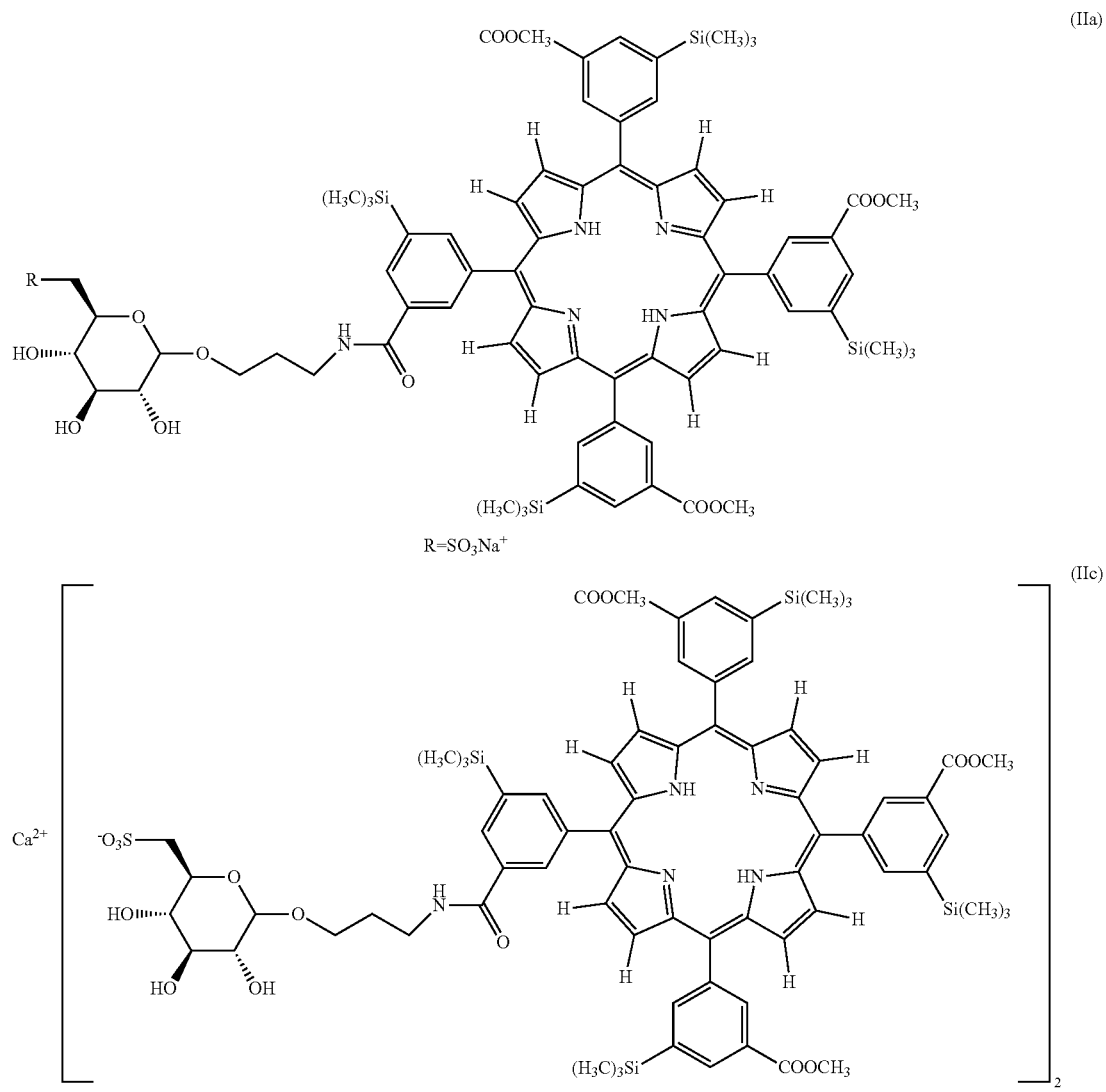

The compounds represented by General Formula (I) above are porphyrin compounds as represented by Structural Formula (III), which will be described later, into which a silicon substituent and a sugar chain are introduced. The compounds represented by General Formula (I) above are more likely to accumulate in tumor sites due to such a configuration. Porphyrin compounds can be used especially as photosensitizing agents for photodynamic therapy in cancer treatment, and can also be used as fluorescent probes because they can emit fluorescence. Accordingly, a composition containing a compound represented by General Formula (I) above can be used as a cancer treatment agent, a photosensitizing agent for photodynamic therapy, or a fluorescent probe composition.

The composition containing a compound represented by General Formula (I) can be administered orally or parenterally (e.g., through local administration, intravenous administration, or the like) in the form of a medicinal preparation such as a tablet, liquid agent, or injection obtained by using the composition as it is or mixing the composition with a pharmacologically acceptable carrier in accordance with a known procedure that is commonly used in methods for producing a medicinal preparation. It should be noted that a compound of General Formula (I) may be administered alone because it is likely to accumulate in a cancer tissue, but alternatively, it may be administered in a form that is likely to reach a target tissue in accordance with a procedure for a drug delivery system (DDS) in which liposome or the like is used.

The content of a compound represented by General Formula (I) in the composition can be selected as appropriate depending on the application thereof, and may be about 0.01 wt % to about 100 wt % of the whole preparation, for example. The dosage amount of a compound of General Formula (I) varies depending on administration targets, target organs, symptoms, administration methods, and the like and is not particularly limited, but a dose thereof is commonly about 0.1 to 1000 mg, and preferably about 1.0 to 100 mg.

Examples of the pharmacologically acceptable carrier include carriers for a solid preparation such as vehicles, lubricants, binders and disintegrators, and carriers for a liquid preparation such as solvents, solubilizing agents, suspending agents, tonicity agents, buffers, and soothing agents. Furthermore, commonly used additives such as antiseptics, antioxidants, coloring agents, sweetening agents, adsorbents, and moistening agents may also be appropriately used in an appropriate amount as needed.

In order to utilize generated singlet oxygen in photodynamic therapy (PDT) or emitted fluorescence in photodynamic diagnosis, the above-mentioned composition containing a compound of General Formula (I) is administered and then irradiated with light of an appropriate wavelength.

The irradiation time is selected as appropriate depending on the age and sex of a patient, the type and extent of disease, a distance between the light source and an affected area, and the like. There is no particular limitation on the wavelength, but a wavelength within a range of 600 nm to 800 nm is preferable. Irradiation may be performed from the outside of the body, or may be performed after an optical fiber or the like is inserted into a portion near a target tissue. An aspect is also encompassed in which bone marrow is extracted from a leukemia patient and treated with a compound of General Formula (I) in vitro, and then the treated bone marrow is returned to the patient.

Generated singlet oxygen can disrupt cells. Moreover, emitted fluorescence can make cells shine. Accordingly, there is no particular limitation on diseases to which the composition according to the present invention can be applied as long as the diseases can be treated due to generated singlet oxygen disrupting cells or can be diagnosed, and examples thereof include cancers, graft-versus-host diseases, graft rejection, autoimmune diseases, T-cell mediated immune allergy, bacterial infectious diseases, viral infection, age-related maculopathy, and acne. Of these, cancers are particularly preferable. There is no particular limitation on the type of cancer, and examples thereof include lung cancer, malignant lymphomas (e.g., reticulosarcoma, lymphosarcoma, Hodgkin's disease, etc.), digestive system cancers (e.g., stomach cancer, gallbladder/bile duct cancer, pancreatic cancer, hepatic cancer, colon cancer, rectal cancer, etc.), breast cancer, ovarian cancer, disseminated multiple myeloma, bladder cancer, leukemia (e.g., acute leukemia including a blast crisis of chronic myelocytic leukemia), renal cancer, and prostatic cancer.

EXAMPLES

Example 1

The following is a description of an example of a method for synthesizing a sodium salt of a compound represented by Structural Formula (IIa) (also represented by Structural Formula (10)). In this example, 3-trimethylsilyl-1-benzenecarboxyamide,N-[3-n-propyl-α-D-quinovopyranoside]-5-[10,15,20-tris(3-carbonate-5-trimethylsilylphenyl)porphyrin] tetrasodium salt (Structural Formula (11)) was synthesized in accordance with Pathways A to G below.

[Chemical Formula 7]

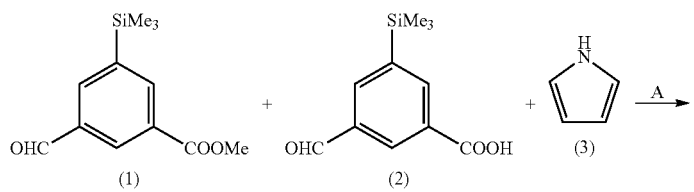

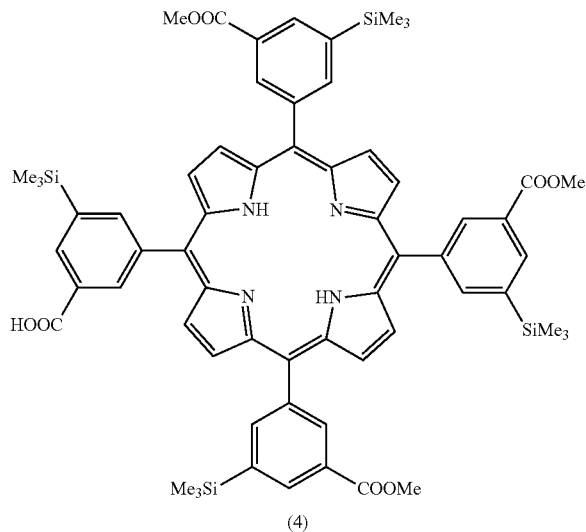

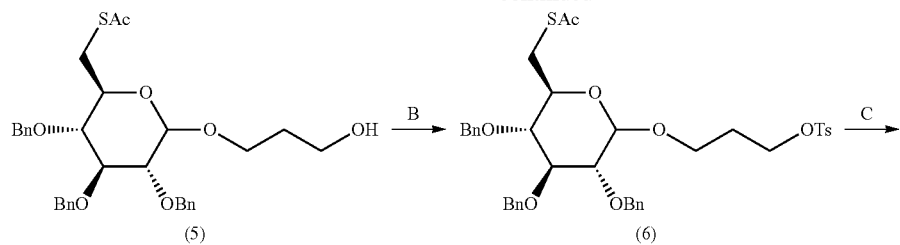
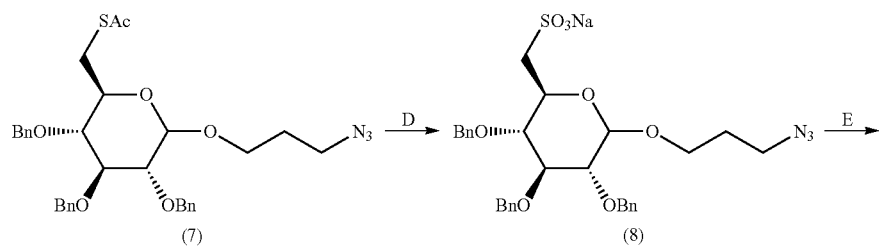
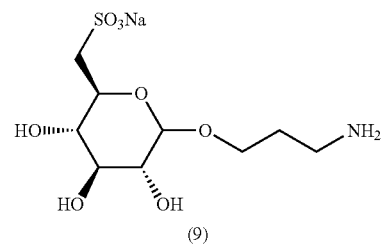
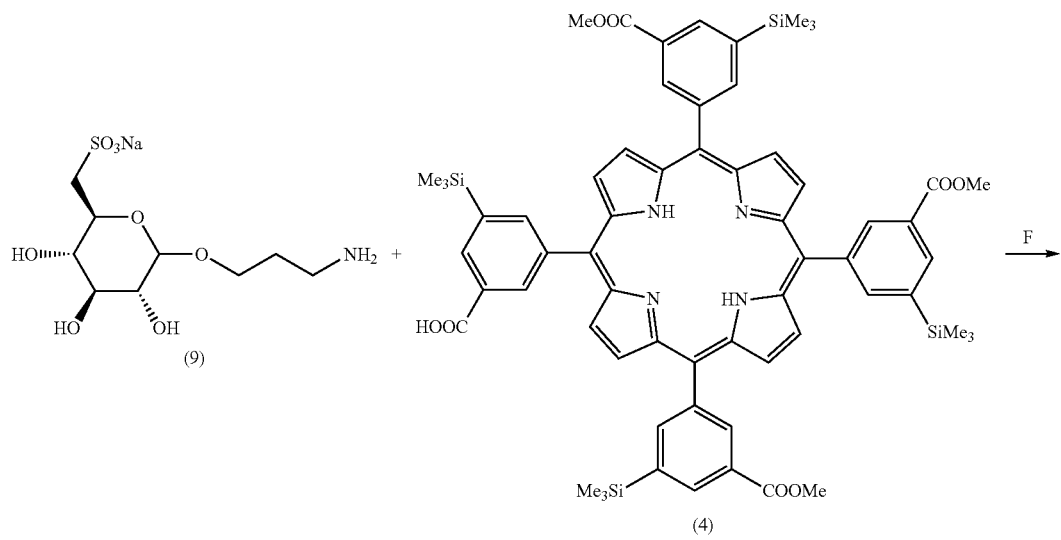

-continued

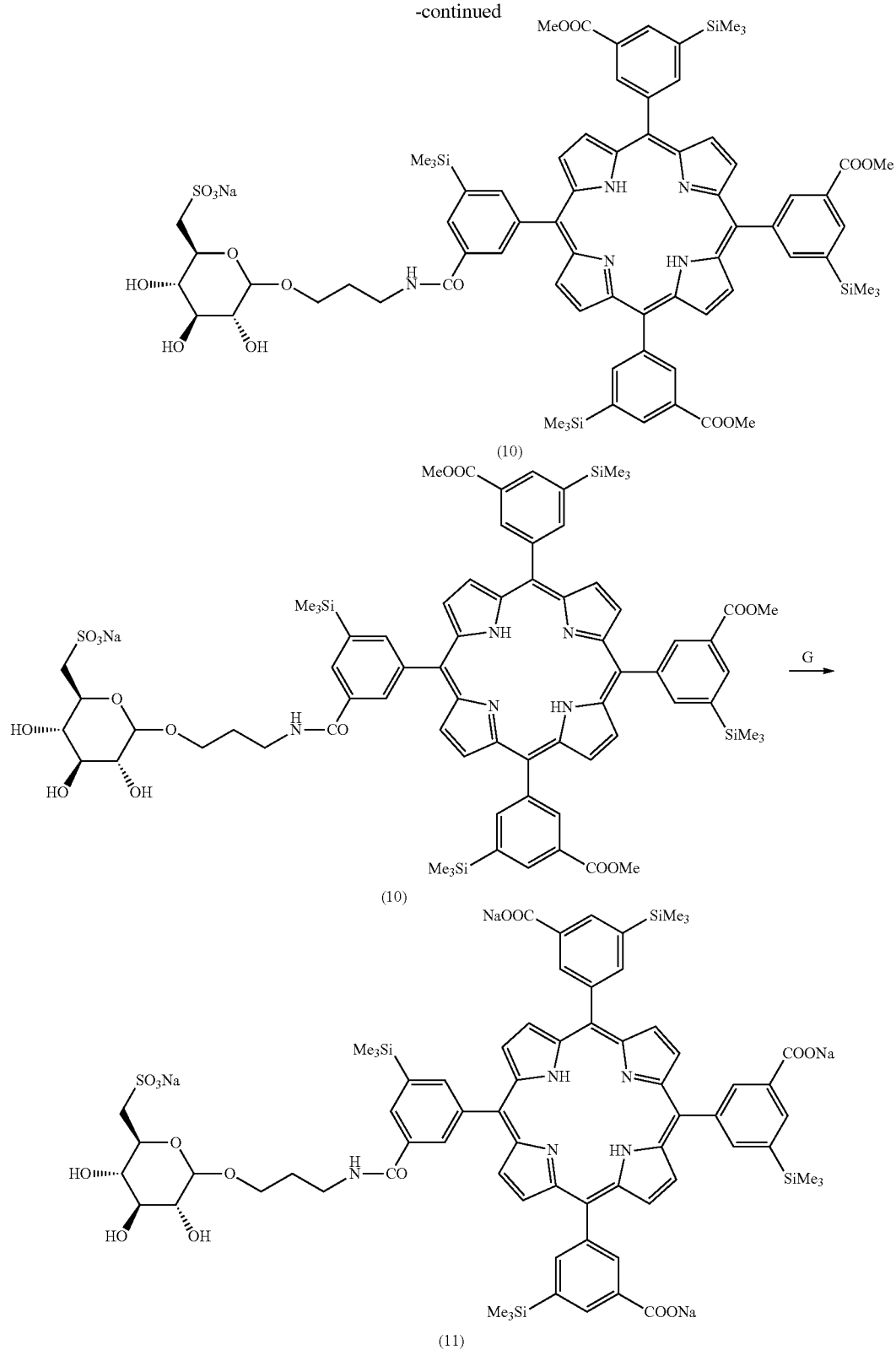

(10)

(10)

(11)

In Pathway A, 5-(3-carboxy-5-trimethylsilylphenyl)-10,15,20-tris(3-methoxycarbonyl-5-trimethylsilylphenyl)porphyrin (Structural Formula (4)) was synthesized. 3-Carboxy-5-trimethylsilylbenzaldehyde methyl ester (Structural Formula (1)) (320 mg), 3-carboxy-5-trimethylsilylbenzaldehyde (Structural Formula (2)) (100 mg) and pyrrole (120 mg) were added to a 200-mL recovery flask. The resultant mixture was dissolved in 50 mL of dehydrated chloroform, and then the recovery flask was purged with nitrogen. Next, a boron fluoride diethyl ether complex was added thereto, and the resultant mixture was stirred at room temperature for 40 minutes. Thereafter, 2,3-dichloro-5,6-dicyano-p-benzoquinone (360 mg) was added thereto, the resultant mixture was reacted at room temperature for 1 hour, and then the solvent was distilled off under reduced pressure. The obtained residue was purified through silica gel column chromatography (hexane/ethyl acetate=66/33, 1% acetic acid solution), and thus a compound represented by Structural Formula (4) was obtained (78.6 mg, 16%).

Figure 6:
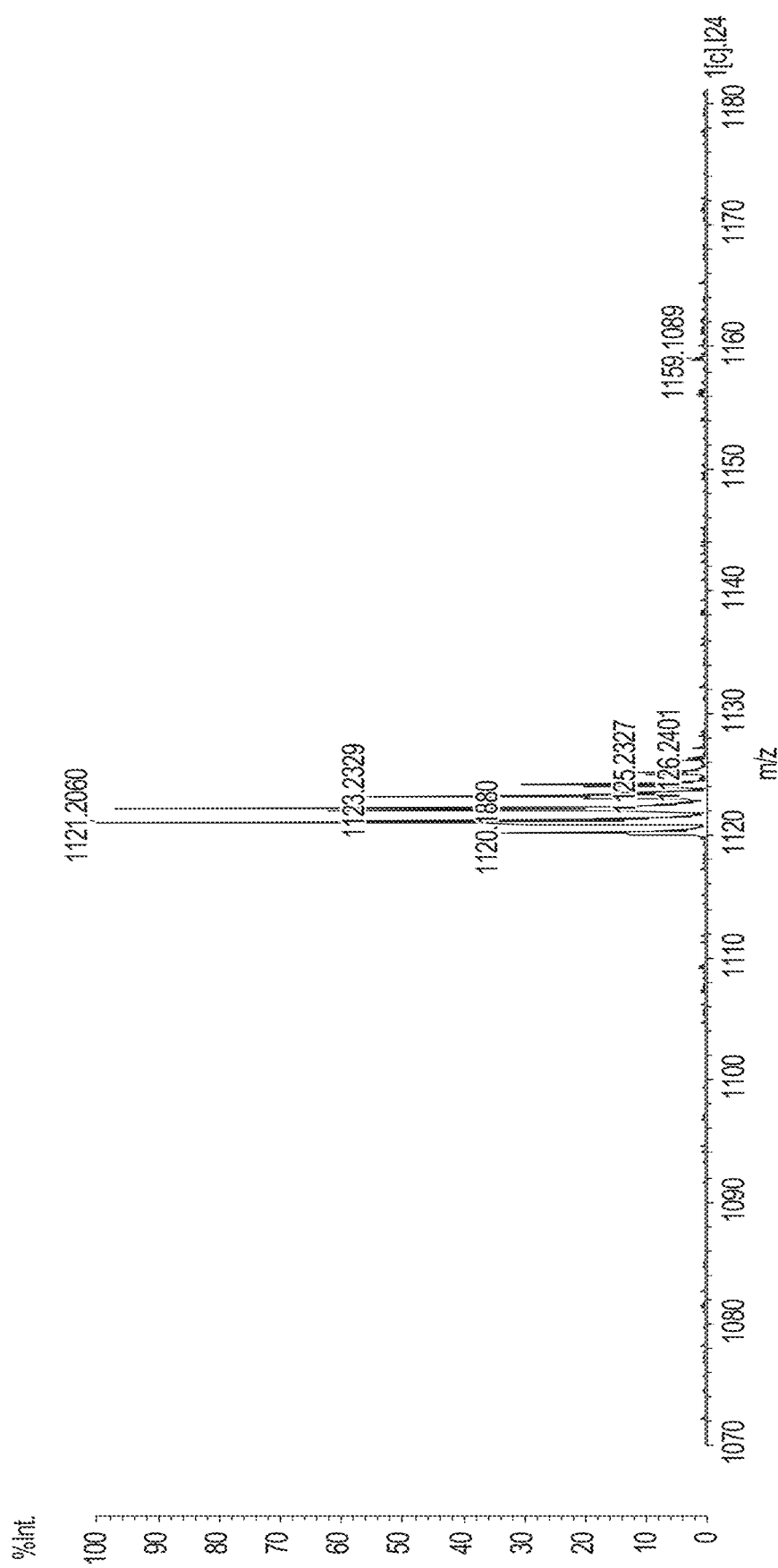
FIG. 6 shows the result of mass spectroscopy of a compound of Structural Formula (4).
Figure 7:
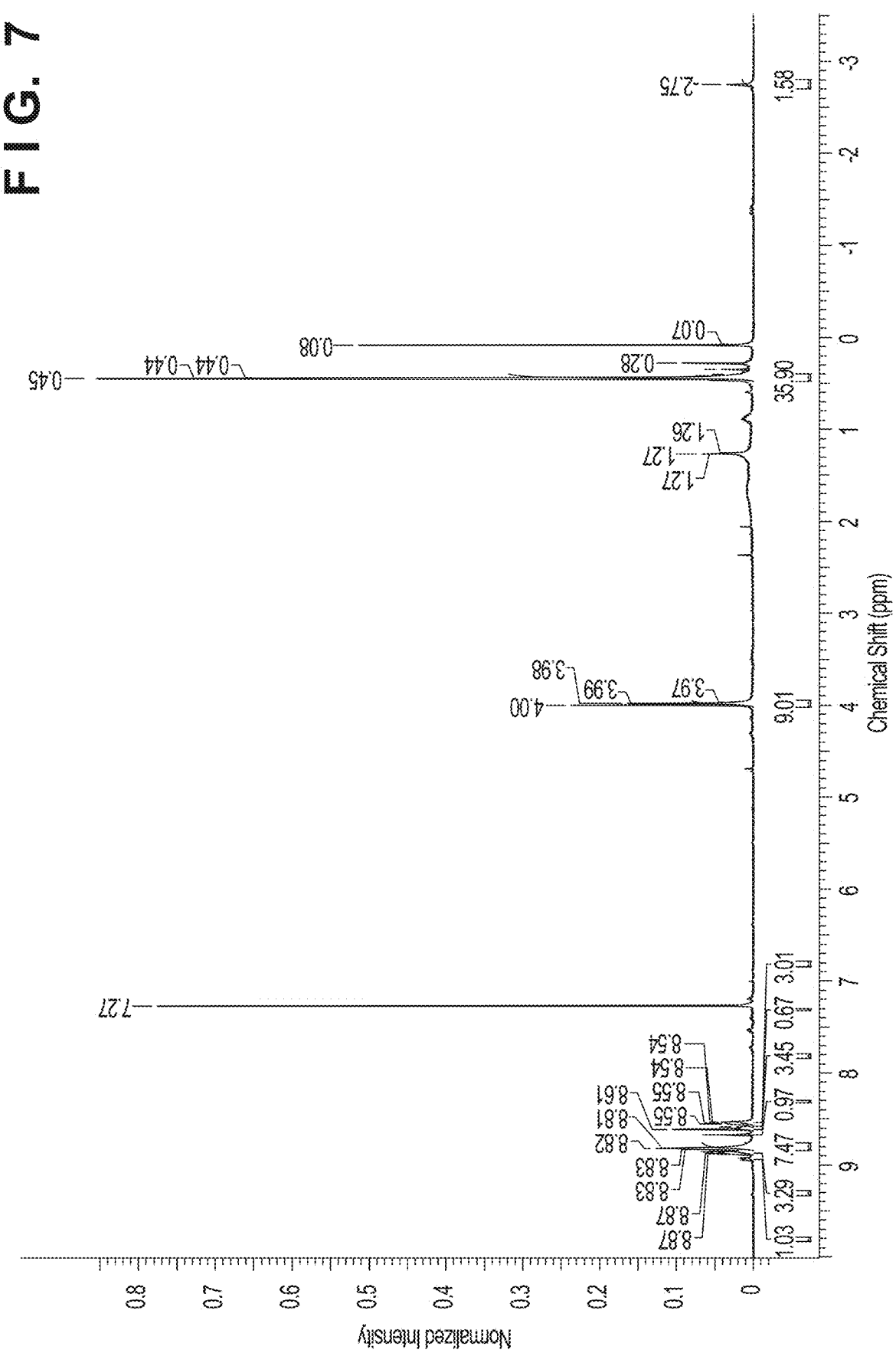
FIG. 7 shows the result of $^1$H-NMR measurement of the compound of Structural Formula (4).

The compound of Structural Formula (4) was subjected to mass spectroscopy and $^1$H-NMR, and the spectra obtained therefrom were shown in FIG. 6 and FIG. 7.

In this example, a mass spectrometer (AXIMA Performance MALDI TOFMS, manufactured by Shimadzu Corporation) was used for mass spectroscopy. In the following description, $^1$H-NMR spectra were measured with a spectrometer (ECS400 400 MHz, manufactured by JEOL) using CDCl$_3$ as a solvent. The following are the data on the spectra obtained through mass spectroscopy and $^1$H-NMR of the compound of Structural Formula (4).

MS: Measured value m/z 1120.19 [M+H], Calculated value 1121.41 [M+H].

δ=8.95-8.93 (d, 1H), 8.88-8.85 (m, 3H), 8.82 (s, 8H), 8.67 (s, 1H), 8.61 (s, 3H), 8.59 (s, 1H), 8.55-8.53 (m, 3H), 4.00 (s, 9H), 0.45 (s, 36H), −2.75 (s, 2H) ppm In Pathway B, 3-(tosyl)-n-propyl2,3,4-tri-O-benzyl-6-thioacetyl-α-D-glucopyranoside (Structural Formula (6)) was synthesized. A 200-mL recovery flask was purged with argon, and dry pyridine (50 mL) was added thereto. 3-(Hydroxy)-n-propyl2,3,4-tri-O-benzyl-6-thioacetyl-α-D-glucopyranoside (Structural Formula (5)) (5 g) and tosyl chloride (5 g) were added thereto under stirring, and then the resultant mixture was stirred at room temperature for 2 hours. Next, ethyl acetate (50 mL) was added to the reaction solution, and the resultant mixture was washed with 1 M hydrochloric acid (1 mL) and was then further washed with a saturated aqueous solution of sodium hydrogen carbonate (1 mL). After dried using magnesium sulfate and filtered, the organic phase was concentrated under reduced pressure, and thus a reaction product was obtained. This reaction product was purified through silica gel chromatography (mixed solution of hexane and ethyl acetate), and thus a compound represented by Structural Formula (6) was obtained (5.0 g, 79%).

Figure 8:
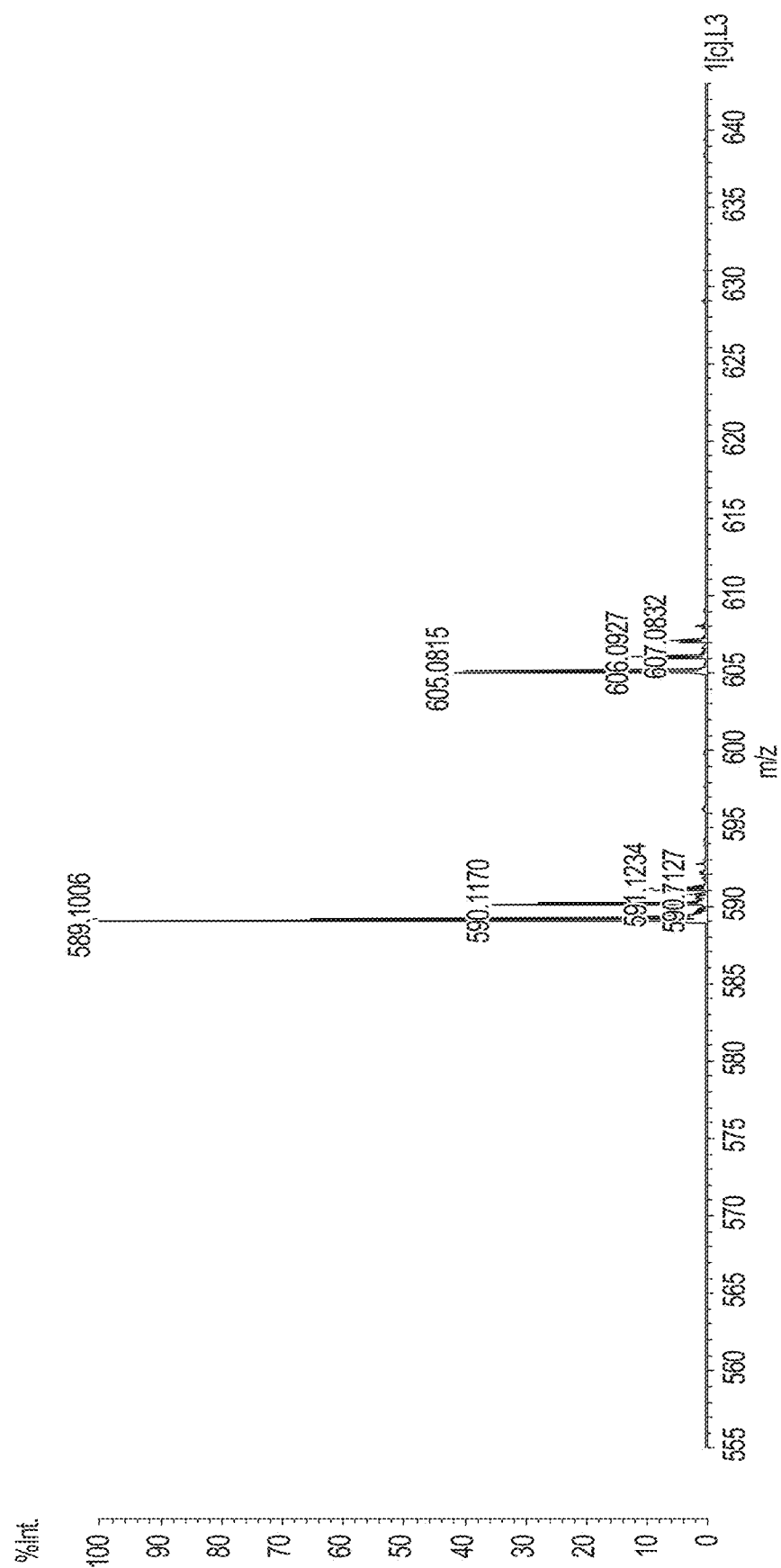
FIG. 8 shows the result of mass spectroscopy of a compound of Structural Formula (5).
Figure 9:
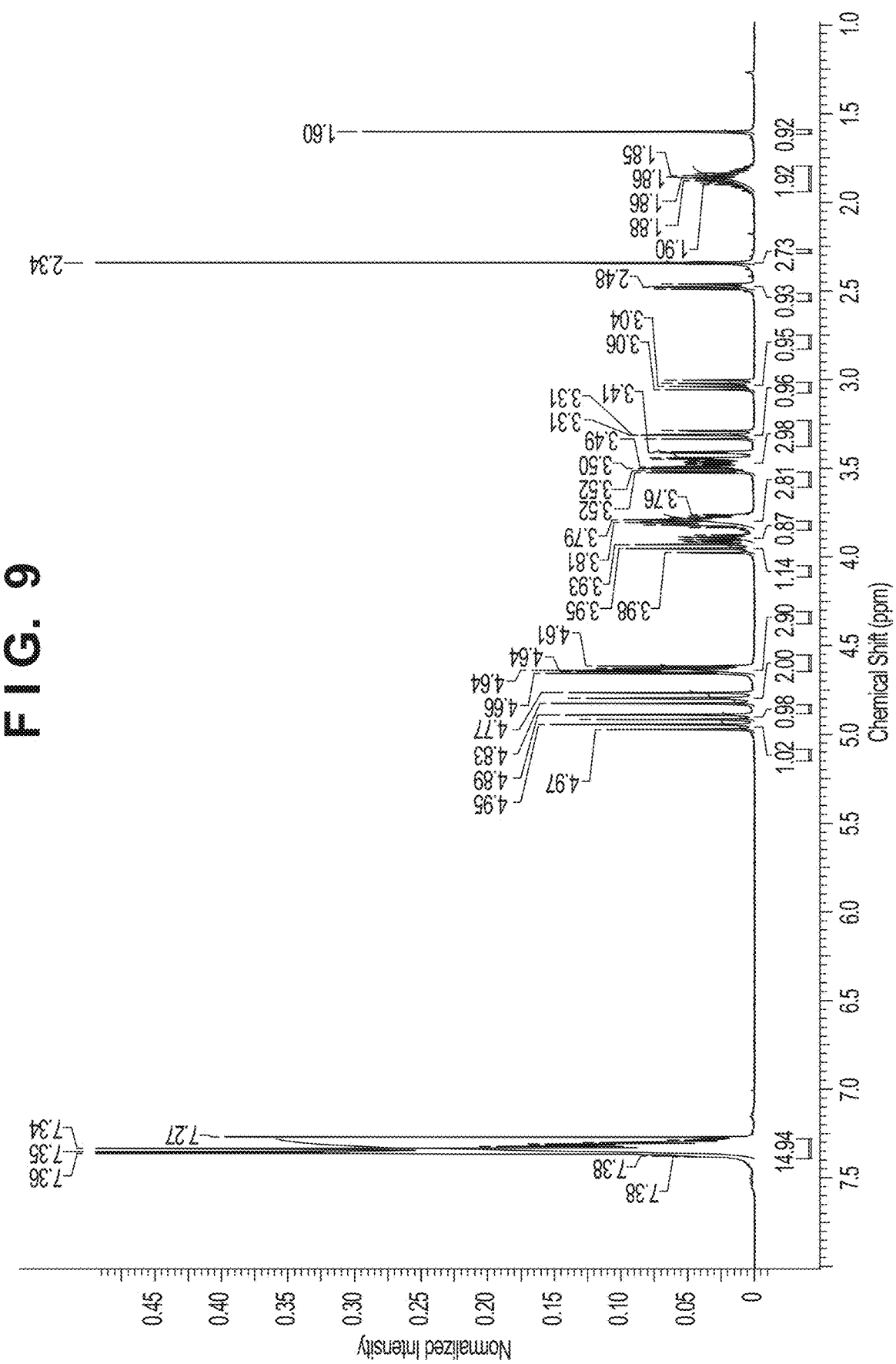
FIG. 9 shows the result of $^1$H-NMR measurement of the compound of Structural Formula (5).
Figure 10:
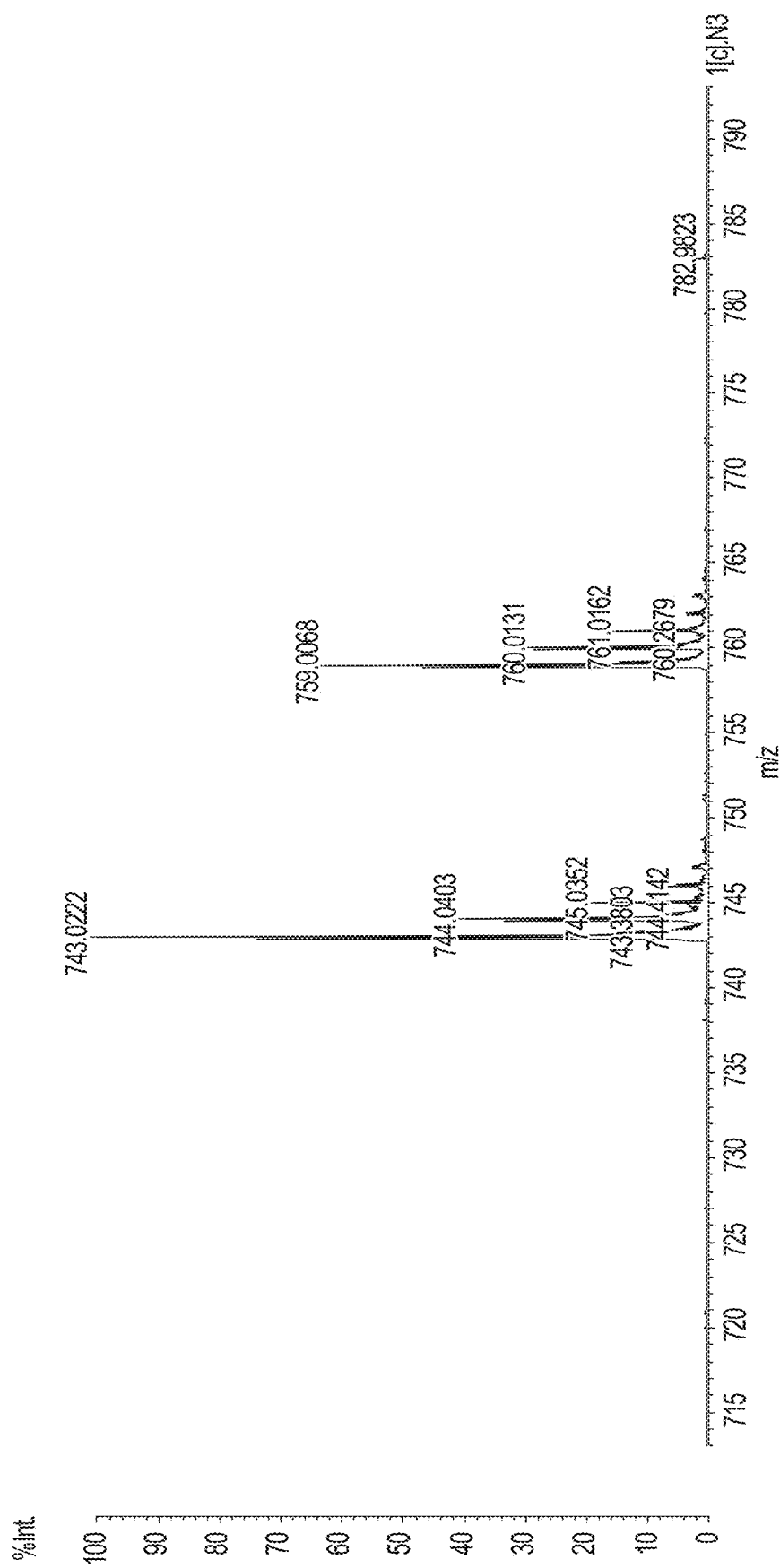
FIG. 10 shows the result of mass spectroscopy of a compound of Structural Formula (6).
Figure 11:
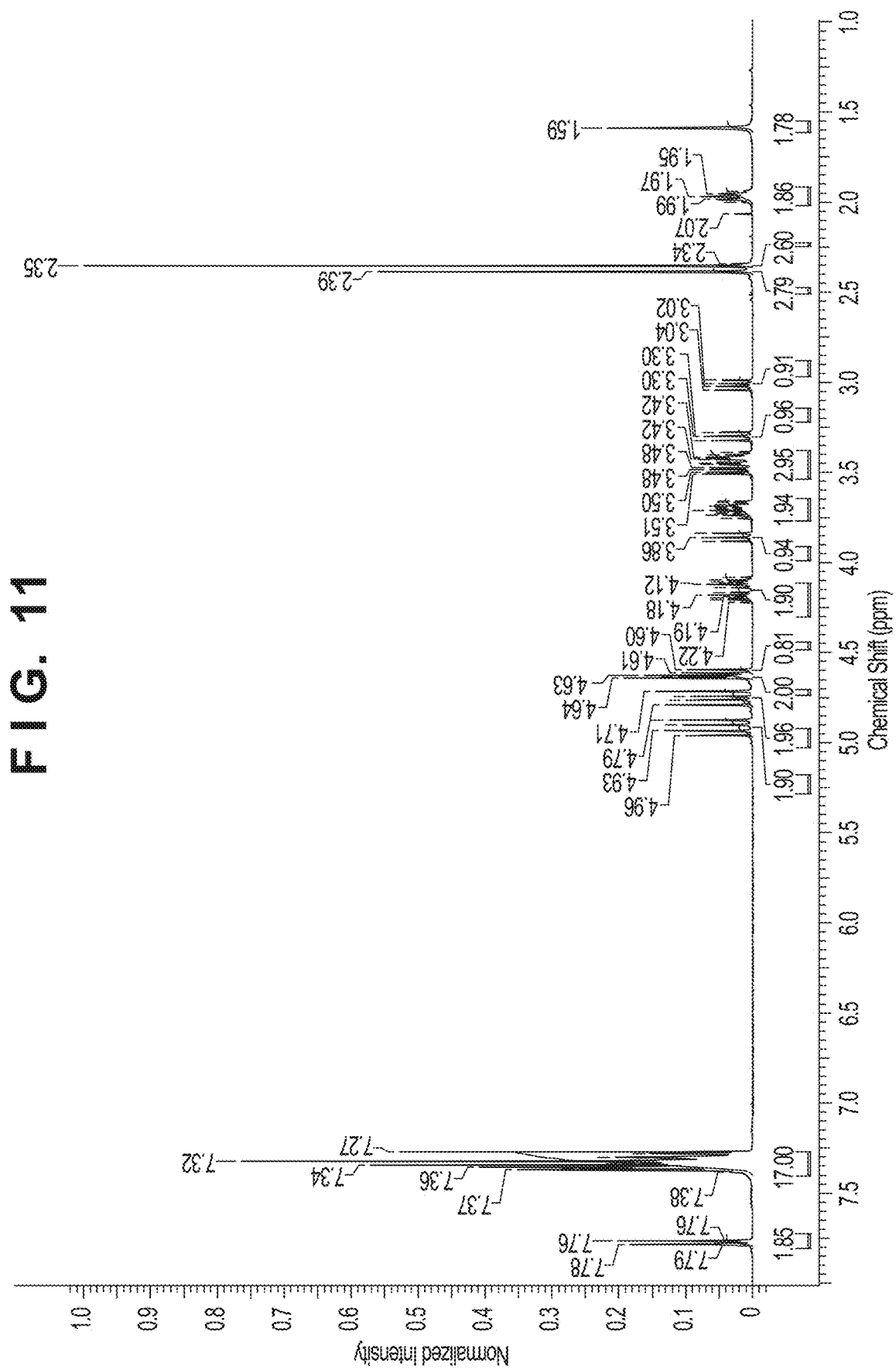
FIG. 11 shows the result of $^1$H-NMR measurement of the compound of Structural Formula (6).

The compound of Structural Formula (5) was subjected to mass spectroscopy and $^1$H-NMR, and the spectra obtained therefrom were shown in FIG. 8 and FIG. 9. Moreover, the compound of Structural Formula (6) was subjected to mass spectroscopy and $^1$H-NMR, and the spectra obtained therefrom were shown in FIG. 10 and FIG. 11.

The following are the data on the spectra obtained through mass spectroscopy and $^1$H-NMR of the compound of Structural Formula (6).

MS: Measured value m/z 743.02 [M+Na], Calculated value 732.24 [M+Na].

δ=7.79-7.76 (d, 2H), 7.38-7.28 (m, 17H), 4.96-4.88 (q, 2H), 4.79-4.71 (q, 2H), 4.64-4.63 (t, 2H), 4.61-4.60 (d, 1H), 4.22-4.08 (m, 2H), 3.88-3.84 (t, 1H), 3.75-3.66 (m, 2H), 3.51-3.39 (m, 3H), 3.32-3.28 (t, 1H), 3.04-2.99 (q, 1H), 2.39 (s, 3H), 2.35 (s, 3H), 2.00-1.94 (m, 2H), 1.59 (s, 2H) ppm In Pathway C, 3-(azide)-n-propyl-2,3,4-tri-O-benzyl-6-thioacetyl-α-D-glucopyranoside (Structural Formula (7)) was synthesized. A 200-mL recovery flask was purged with argon, and dry dimethylformamide (50 mL) was added thereto. The compound of Structural Formula (6) (3.6 g) and sodium azide (3.6 g) were added thereto under stirring, and the resultant mixture was stirred at 50° C. for 3 hours. Ethyl acetate (50 mL) was added to the reaction solution, and the resultant mixture was washed with a saturated aqueous solution of sodium hydrogen carbonate (50 mL) and was then further washed with saturated saline (50 mL). After dried using magnesium sulfate and filtered, the organic phase was concentrated under reduced pressure to obtain a reaction product. This reaction product was purified through silica gel chromatography (mixed solution of hexane and ethyl acetate), and thus a compound represented by Structural Formula (7) was obtained (2.3 g, 79%).

Figure 12:
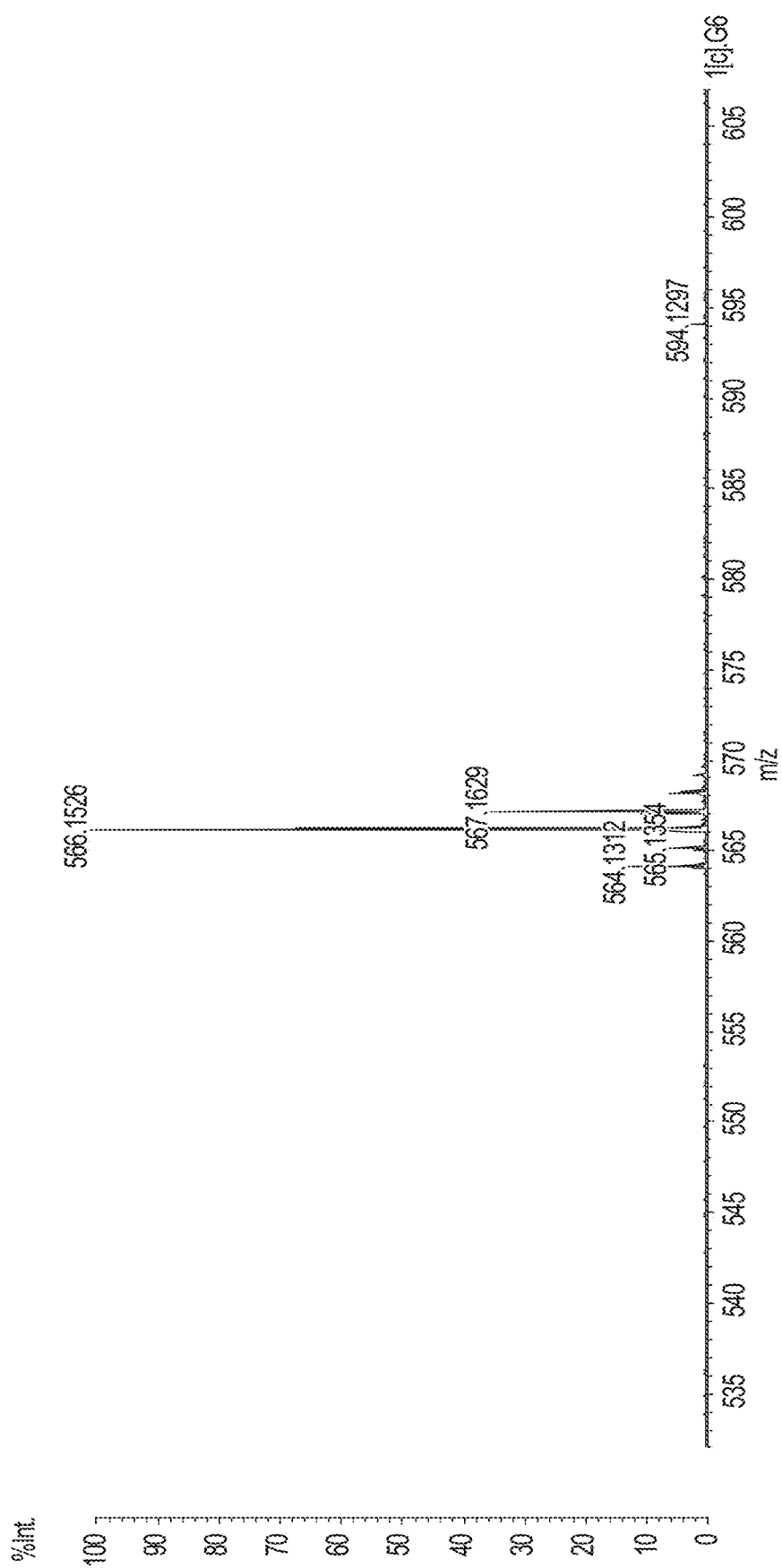
FIG. 12 shows the result of mass spectroscopy of a compound of Structural Formula (7).
Figure 13:
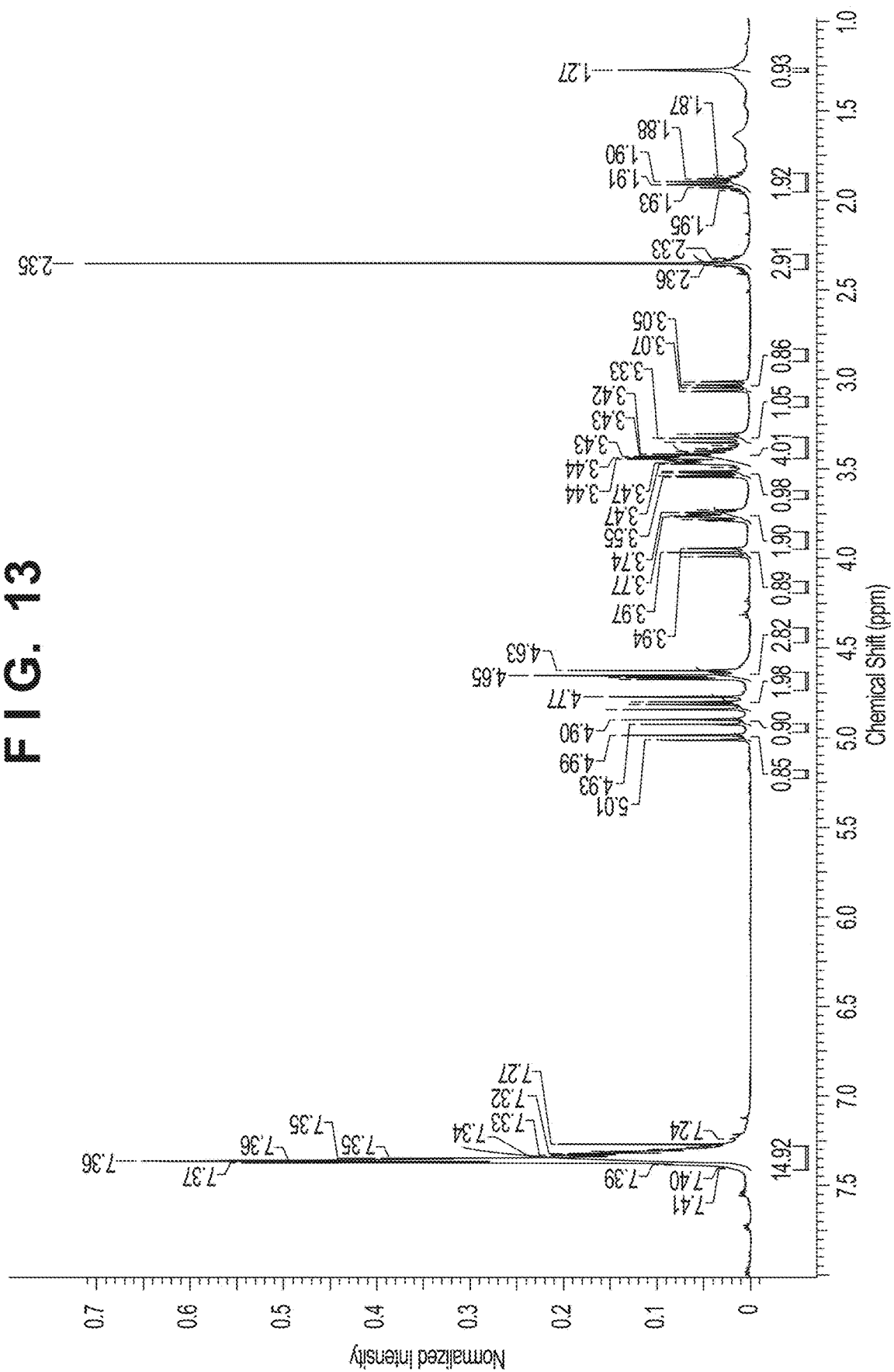
FIG. 13 shows the result of $^1$H-NMR measurement of the compound of Structural Formula (7).

The compound of Structural Formula (7) was subjected to mass spectroscopy and $^1$H-NMR, and the spectra obtained therefrom were shown in FIG. 12 and FIG. 13.

The following are the data on the spectra obtained through mass spectroscopy and $^1$H-NMR of the compound of Structural Formula (7).

MS: Measured value m/z 564.13 [M−N$_2$+H], Calculated value 564.24 [M−N$_2$+H], Mathematical formula $C_{32}H_{37}N_3O_6S$ δ=7.41-7.29 (m, 15H), 5.01-4.99 (d, 1H), 4.93-4.90 (d, 1H), 4.84-4.77 (q, 2H), 4.67-4.63 (m, 3H), 3.99-3.94 (t, 1H), 3.79-3.73 (m, 2H), 3.55-3.51 (q, 1H), 3.47-3.37 (m, 4H), 3.35-3.31 (t, 1H), 3.07-3.01 (q, 1H), 2.35 (s, 3H), 1.95-1.87 (m, 2H), 1.27 (s, 1H) ppm In Pathway D, 3-(azide)-n-propyl2,3,4-tri-O-benzyl-α-D-quinovopyranoside sodium salt (Structural Formula (8)) was synthesized. After a 200-mL recovery flask was purged with argon, the compound of Structural Formula (7) (2.2 g), potassium acetate (7.4 g), oxone (5.8 g), and acetic acid (50 mL) were added thereto, and the resultant mixture was stirred at room temperature under an argon atmosphere for 2 days. Ethyl acetate (50 mL) was added to the reaction solution, and the resultant mixture was washed with a saturated aqueous solution of sodium hydrogen carbonate (50 mL). After dried using magnesium sulfate and filtered, the organic phase was concentrated under reduced pressure, and thus a reaction product was obtained. This reaction product was purified through silica gel chromatography (mixed solution of chloroform and methanol), and thus a compound represented by Structural Formula (8) was obtained (1.8 g, 80%).

Figure 14:
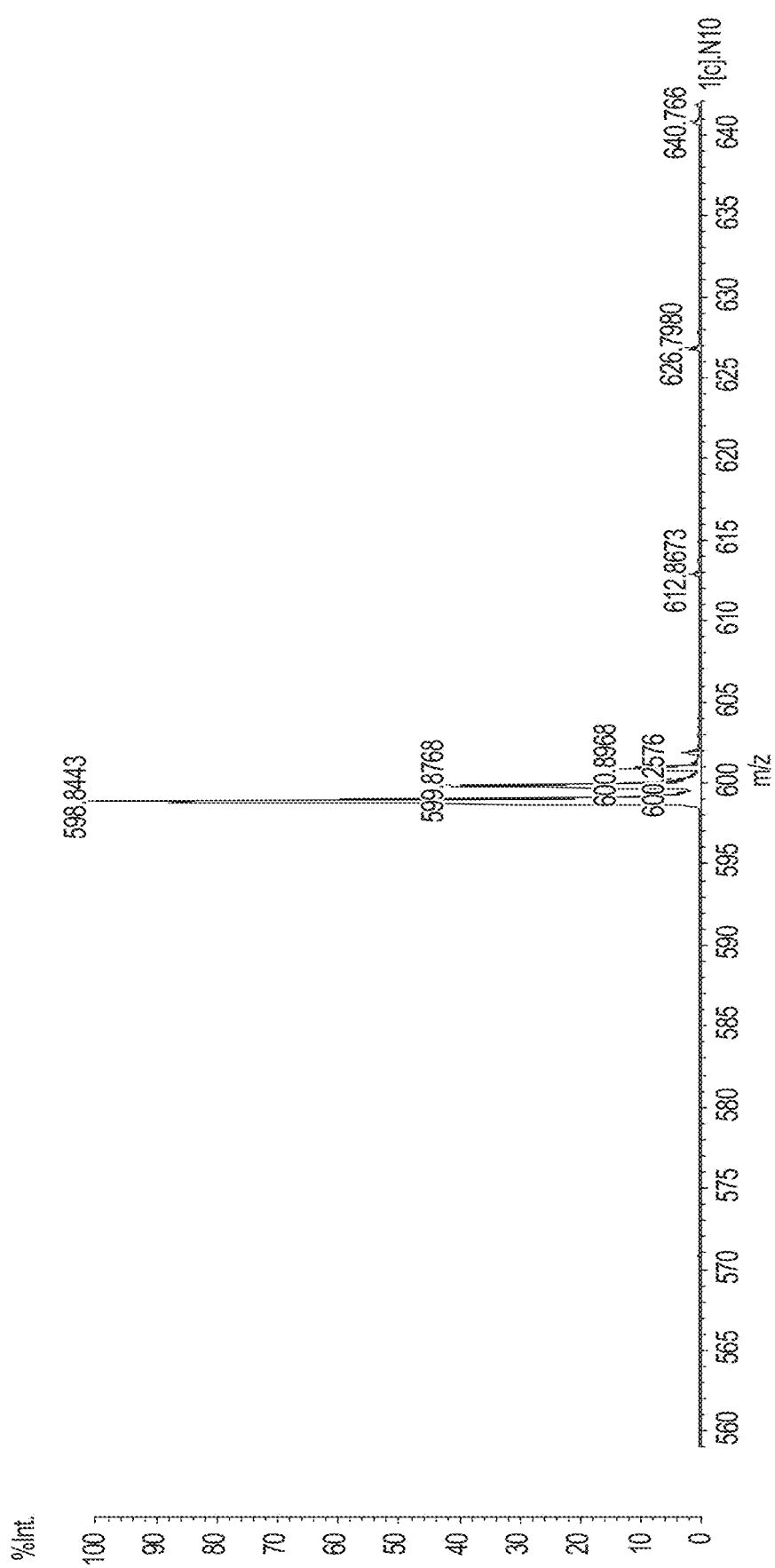
FIG. 14 shows the result of mass spectroscopy of a compound of Structural Formula (8).
Figure 15:
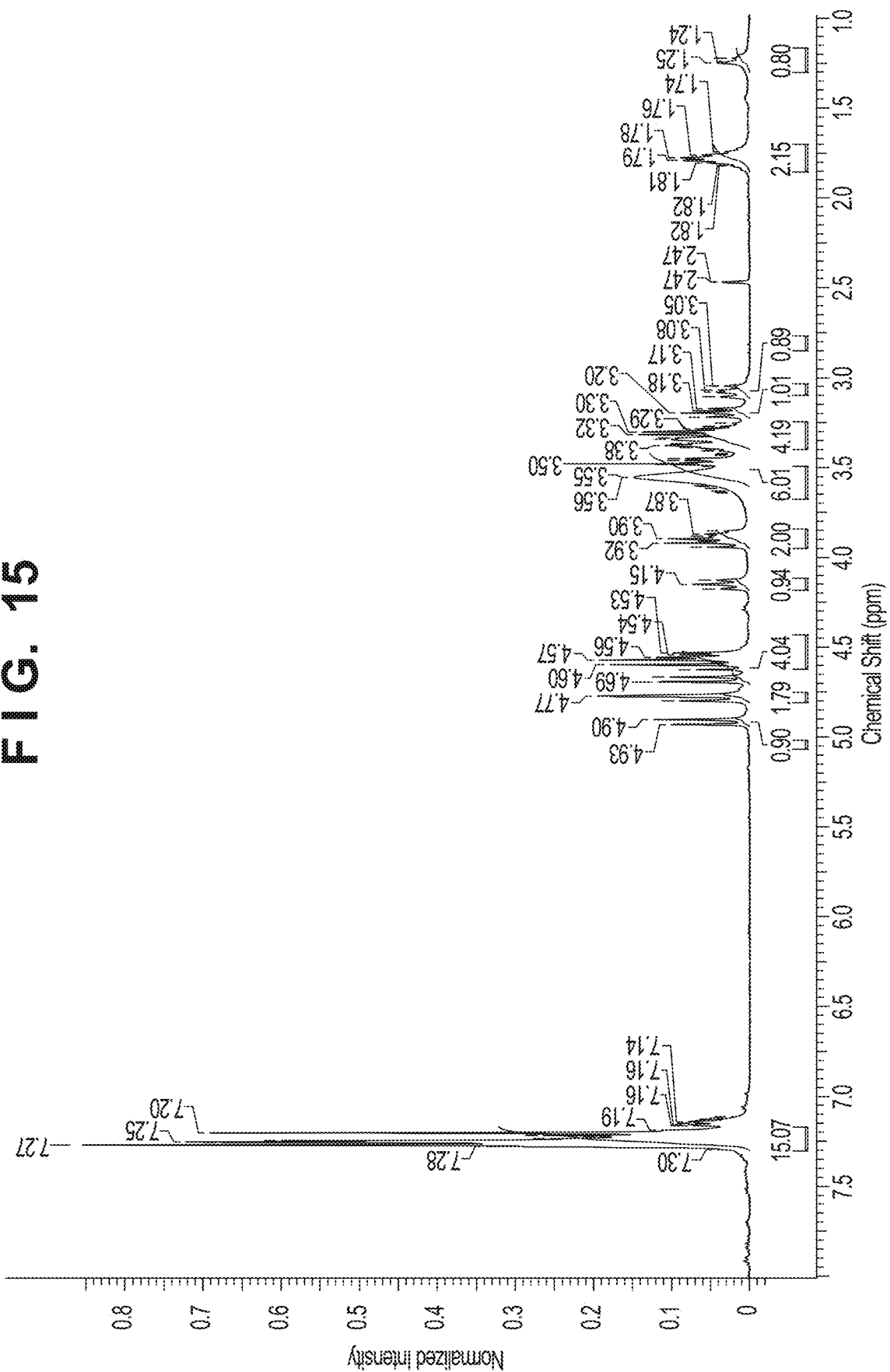
FIG. 15 shows the result of $^1$H-NMR measurement of the compound of Structural Formula (8).

The compound of Structural Formula (8) was subjected to mass spectroscopy and $^1$H-NMR, and the spectra obtained therefrom were shown in FIG. 14 and FIG. 15.

The following are the data on the spectra obtained through mass spectroscopy and $^1$H-NMR of the compound of Structural Formula (8).

MS: Measured value m/z 598.84 [M−Na+H$_2$], Calculated value 598.21 [M−Na+H$_2$], Mathematical formula $C_{30}H_{34}N_3NaO_8S$ δ=7.30-7.19 (m, 15H), 4.93-4.90 (d, 1H), 4.80-4.77 (d, 2H), 4.69-4.53 (m, 4H), 4.18-4.13 (t, 1H), 3.94-3.86 (m, 2H), 3.63-3.43 (m, 6H), 3.41-3.25 (m, 4H), 3.22-3.17 (t, 1H), 3.11-3.05 (q, 1H), 1.82-1.74 (m, 2H), 1.25-1.22 (m, 1H) ppm In Pathway E, 3-(amino)-n-propyl-α-D-quinovopyranoside sodium salt (Structural Formula (9)) was synthesized. The compound of Structural Formula (8) (1.2 g), palladium hydroxide (1.9 g), tert-butanol (40 mL), and water (40 mL) were added to a 200-mL recovery flask, and the resultant mixture was stirred at 40° C. under a hydrogen atmosphere overnight. This reaction solution was concentrated under reduced pressure, and thus a reaction product was obtained. The reaction product was purified through reversed phase silica gel chromatography (mixed solution of water and methanol), and thus a compound represented by Structural Formula (9) was obtained (0.53 g, 85%).

Figure 16:
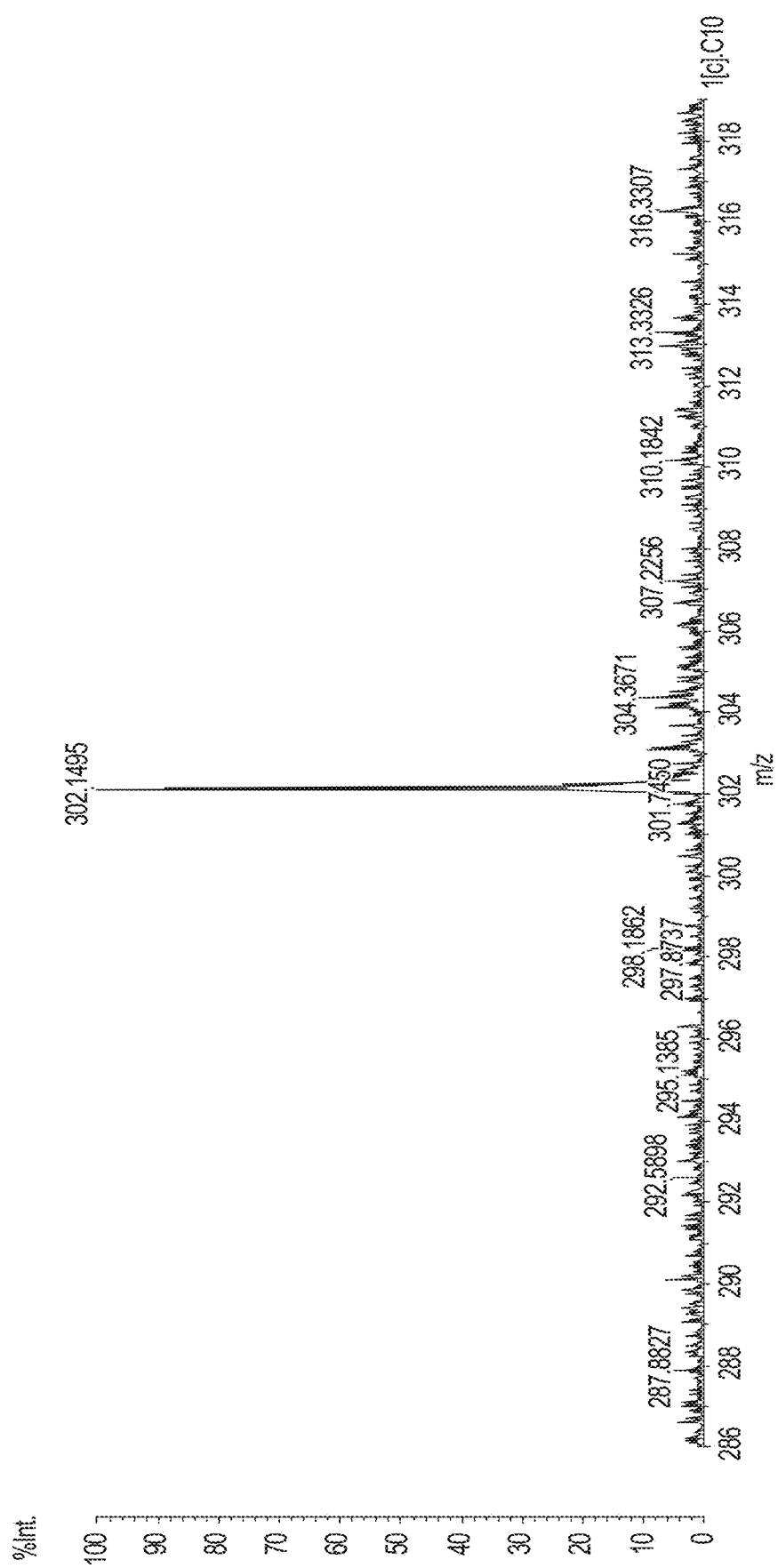
FIG. 16 shows the result of mass spectroscopy of a compound of Structural Formula (9).
Figure 17:
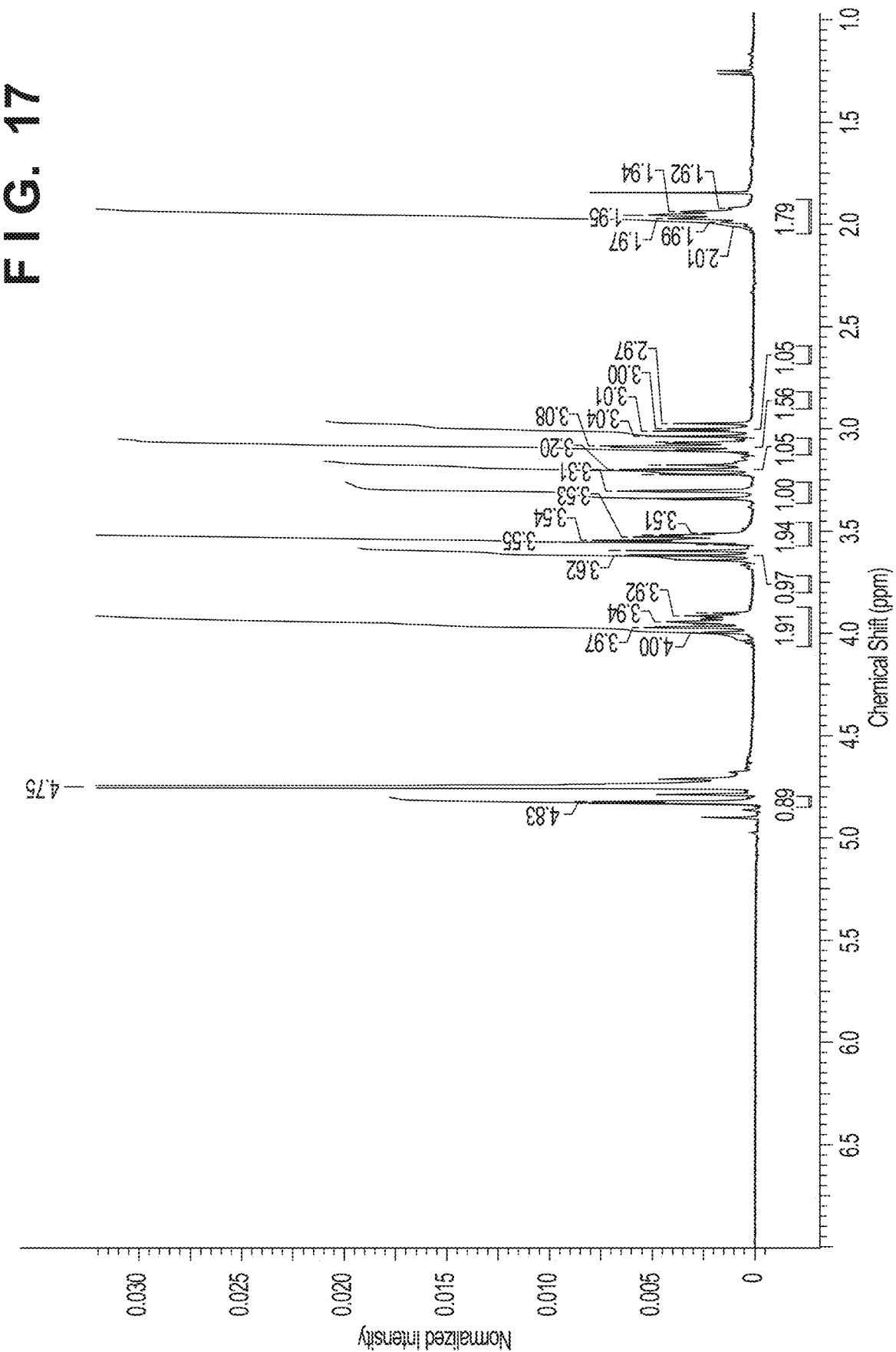
FIG. 17 shows the result of $^1$H-NMR measurement of the compound of Structural Formula (9).

The compound of Structural Formula (9) was subjected to mass spectroscopy and $^1$H-NMR, and the spectra obtained therefrom were shown in FIG. 16 and FIG. 17.

The following are the data on the spectra obtained through mass spectroscopy and $^1$H-NMR of the compound of Structural Formula (9).

MS: Measured value m/z 302.15 [M−Na+H$_2$], Calculated value 302.08 [M−Na+H$_2$], Mathematical formula C$_9$H$_{19}$NNaO$_8$S δ=4.80-4.79 (d, 1H), 3.97-3.86 (m, 2H), 3.62-3.54 (q, 1H), 3.52-3.47 (m, 2H), 3.31-3.26 (d, 1H), 3.20-3.13 (t, 1H), 3.08-3.04 (t, 2H), 3.01-2.93 (q, 1H), 1.97-1.88 (m, 2H) ppm In Pathway F, 3-trimethylsilyl-1-benzenecarboxyamide, N-[3-n-propyl-α-D-quinovopyranoside]-5-[10,15,20-tris(3-methoxycarbonyl-5-trimethylsilylphenyl)porphyrin] sodium salt (Structural Formula (10)) was synthesized. The compound of Structural Formula (4) (10 mg), the compound of Structural Formula (9) (9.1 mg), 1-(3-dimethylaminopropyl)-3-ethylcarbodiimide hydrochloride (3.5 mg), 1-hydroxybenzotriazole (3.6 mg), diethylaniline (25 μL), and dimethylformamide (1.6 mL) were added to a 50-mL recovery flask. Next, this mixed solution was stirred at room temperature for 13 hours. Ethyl acetate (50 mL) was added to this reaction solution, and the resultant mixture was washed with a saturated aqueous solution of sodium hydrogen carbonate (50 mL) and was then further washed with saturated saline (50 mL). After dried using magnesium sulfate and filtered, the organic phase was concentrated under reduced pressure, and thus a reaction product was obtained. This reaction product was purified through silica gel chromatography (mixed solution of dichloromethane and methanol), and thus a compound represented by Structural Formula (10) was obtained (9.8 mg, 80%).

Figure 18:
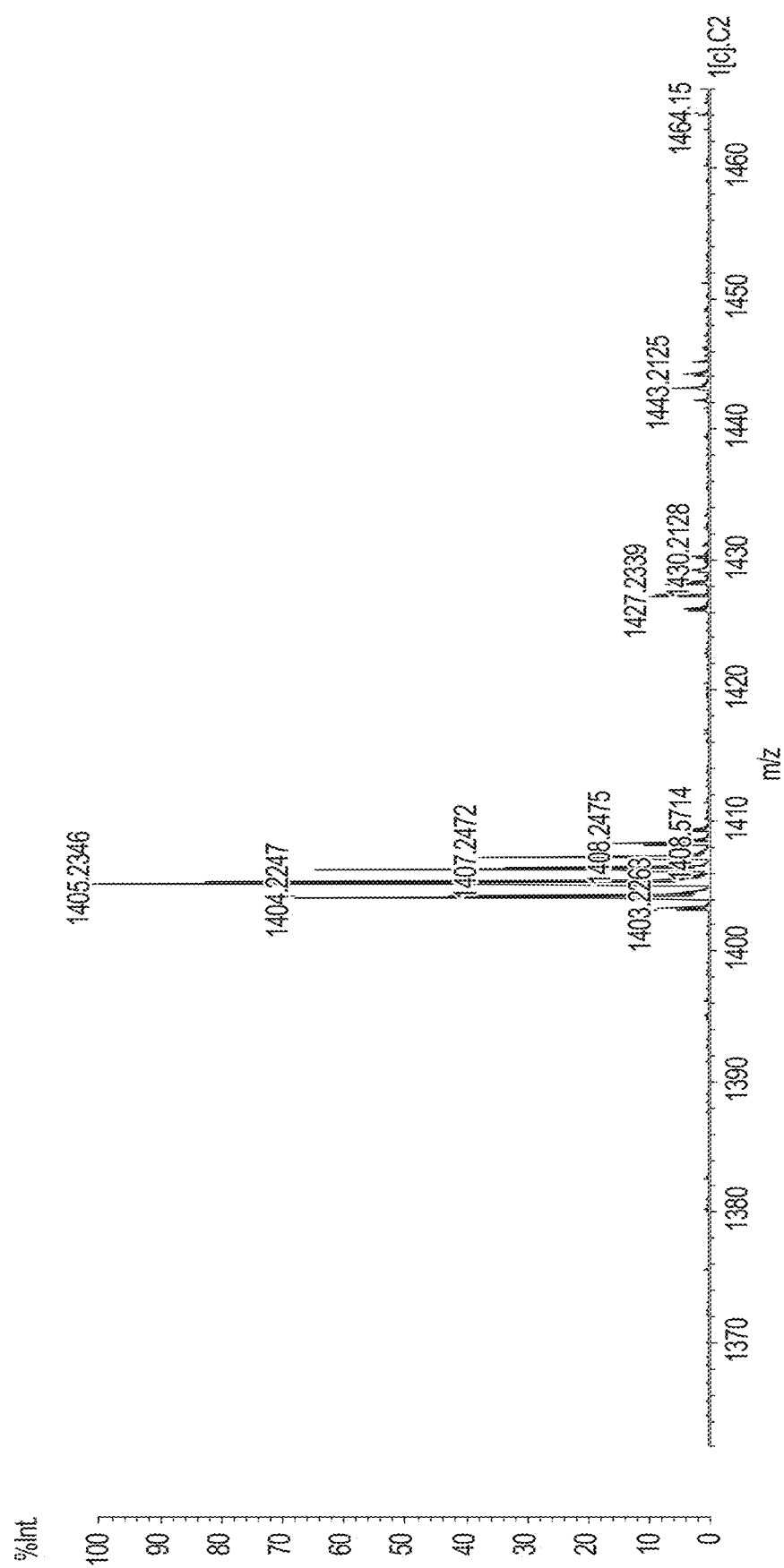
FIG. 18 shows the result of mass spectroscopy of a compound of Structural Formula (10).
Figure 19:
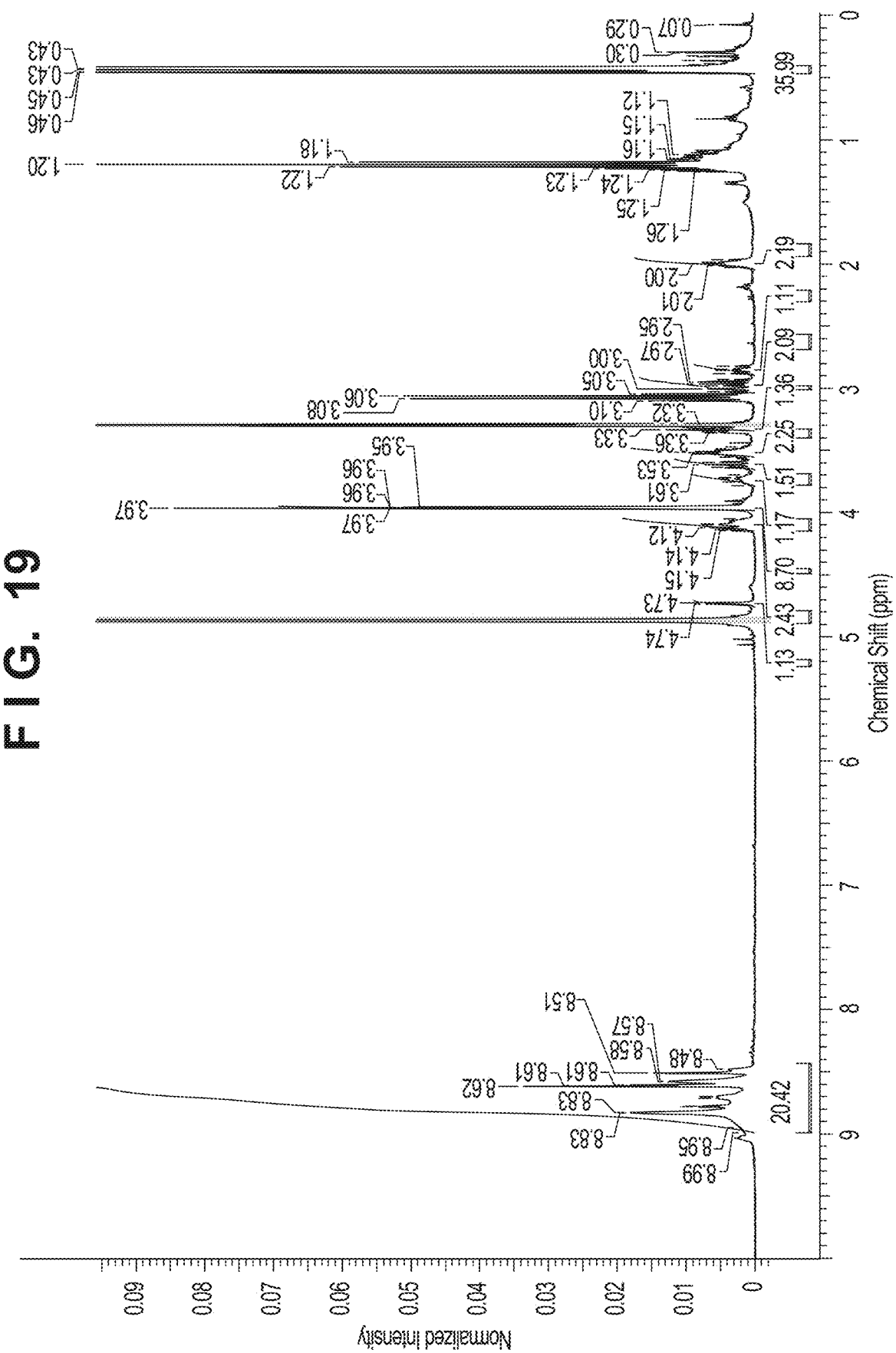
FIG. 19 shows the result of $^1$H-NMR measurement of the compound of Structural Formula (10).

The compound of Structural Formula (10) was subjected to mass spectroscopy and $^1$H-NMR, and the spectra obtained therefrom were shown in FIG. 18 and FIG. 19.

The following are the data on the spectra obtained through mass spectroscopy and $^1$H-NMR of the compound of Structural Formula (10).

MS: Measured value m/z 1404.22 [M−Na+H$_2$], Calculated value 1404.48 [M−Na+H$_2$], Mathematical formula C$_{72}$H$_{85}$N$_5$NaO$_{15}$SSi$_4$ δ=8.99-8.48 (br, 20H), 4.74-4.73 (m, 1H), 4.15-4.05 (m, 2H), 3.97 (s, 9H), 3.78-3.70 (m, 1H), 3.64-3.59 (t, 2H), 3.55-3.49 (m, 2H), 3.35-3.32 (m, 1H), 3.03-2.93 (m, 2H), 2.88-2.82 (q, 1H), 2.03-1.96 (m, 2H), 0.46-0.42 (m, 36H) ppm In Pathway G, 3-trimethylsilyl-1-benzenecarboxyamide, N-[3-n-propyl-α-D-quinovopyranoside]-5-[10,15,20-tris(3-carbonate-5-trimethylsilylphenyl)porphyrin] tetrasodium salt (Structural Formula (11)) was synthesized. The compound of Structural Formula (10) (17 mg), a 1 M aqueous solution of sodium hydroxide (150 μL), tetrahydrofuran (2 mL), and methanol (1 mL) were added to a 50-mL recovery flask, and the resultant mixture was stirred at 40° C. for 3 hours. This reaction solution was concentrated under reduced pressure, and thus a reaction product was obtained. The reaction product was purified through reversed phase silica gel chromatography (mixed solution of water and methanol) and was then purified through gel filtration (methanol), and thus a compound represented by Structural Formula (11) was obtained (14 mg, 80%).

Figure 20:
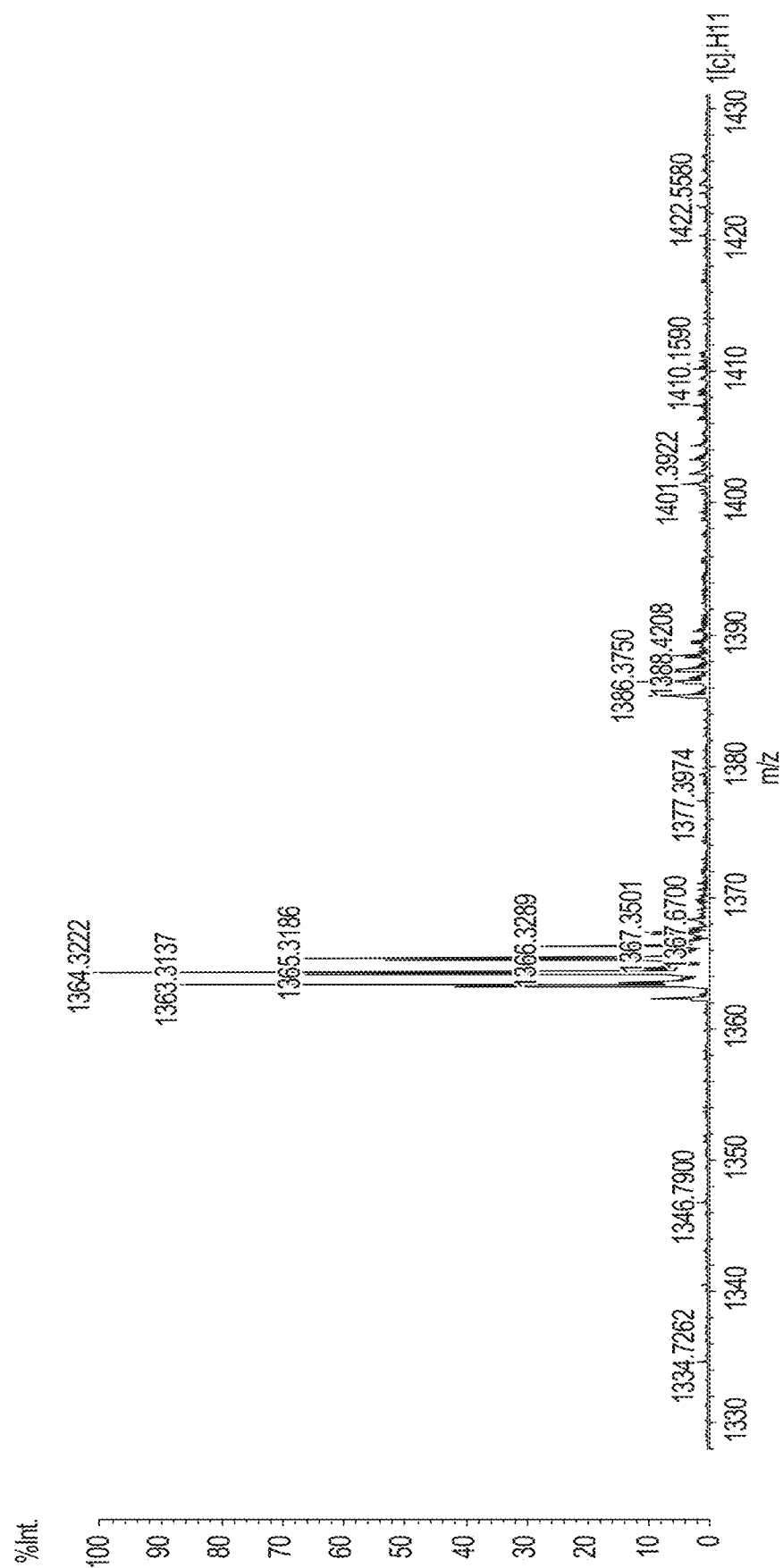
FIG. 20 shows the result of mass spectroscopy of a compound of Structural Formula (11).
Figure 21:
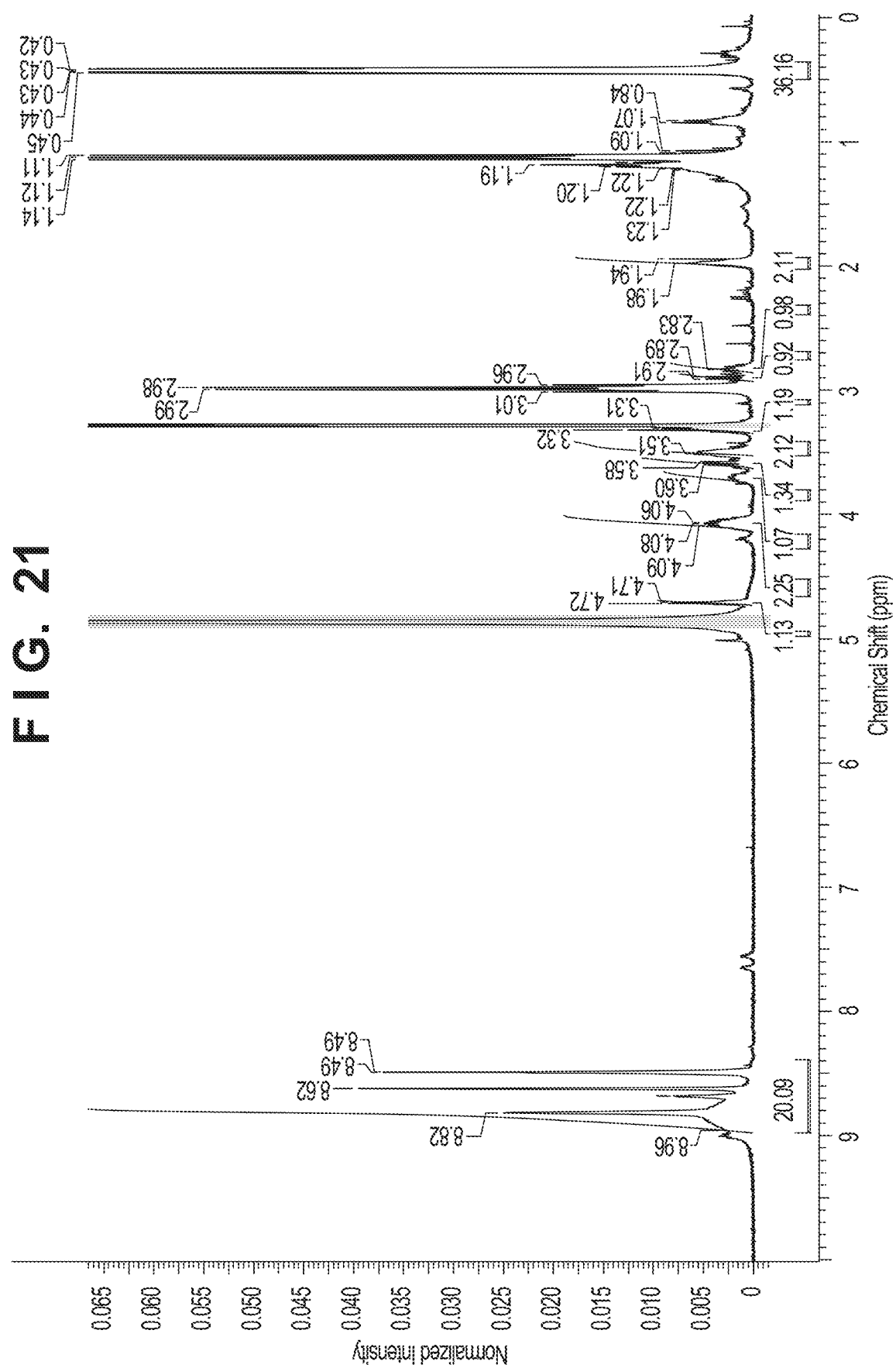
FIG. 21 shows the result of $^1$H-NMR measurement of the compound of Structural Formula (11).

The compound of Structural Formula (11) was subjected to mass spectroscopy and $^1$H-NMR, and the spectra obtained therefrom were shown in FIG. 20 and FIG. 21.

The following are the data on the spectra obtained through mass spectroscopy and $^1$H-NMR of the compound of Structural Formula (11).

MS: Measured value m/z 1363.31 [M−Na$_4$+H$_5$], Calculated value 1362.44 [M−Na$_4$+H$_5$], Mathematical formula C$_{69}$H$_{75}$N$_5$Na$_4$O$_{15}$SSi$_4$ δ=8.96-8.49 (br, 20H), 4.72-4.70 (m, 1H), 4.13-4.03 (m, 2H), 3.75-3.66 (m, 1H), 3.63-3.55 (m, 1H), 3.52-3.42 (m, 2H), 3.34-3.30 (m, 1H), 2.93-2.87 (q, 1H), 2.85-2.80 (m, 1H), 1.98 (br, 2H), 0.45-0.41 (m, 36H) ppm Example 2

The following is a description of an example of a method for synthesizing 3-trimethylsilyl-1-benzenecarboxyamide, N-[3-n-propyl-α-D-glucopyranoside]-5-[10,15,20-tris(3-carbonate-5-trimethylsilylphenyl)porphyrin]trisodium salt (represented by Structural Formula (17) below), which is an aspect of a photosensitizing agent according to the present invention. In this embodiment, the compound represented by Structural Formula (17) was synthesized in accordance with Pathways H to L below.

[Chemical Formula 8]

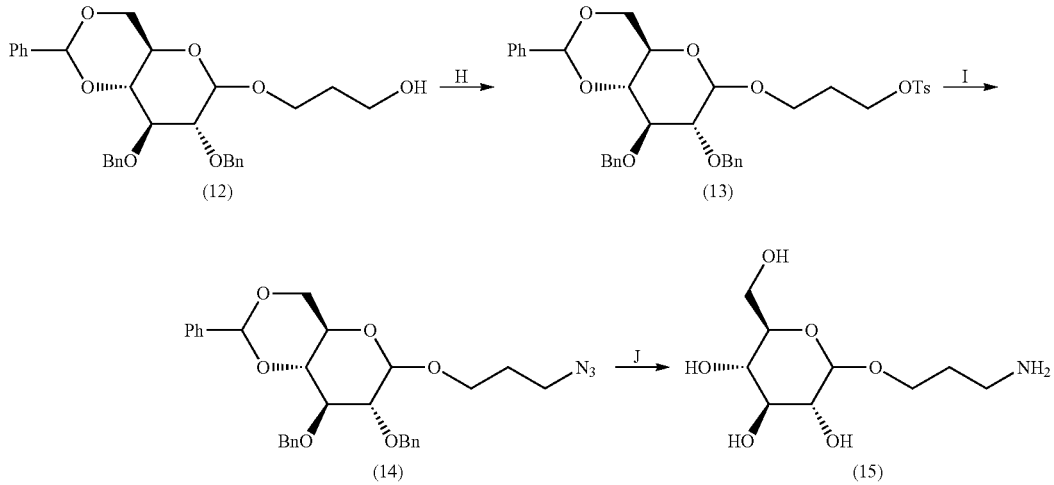

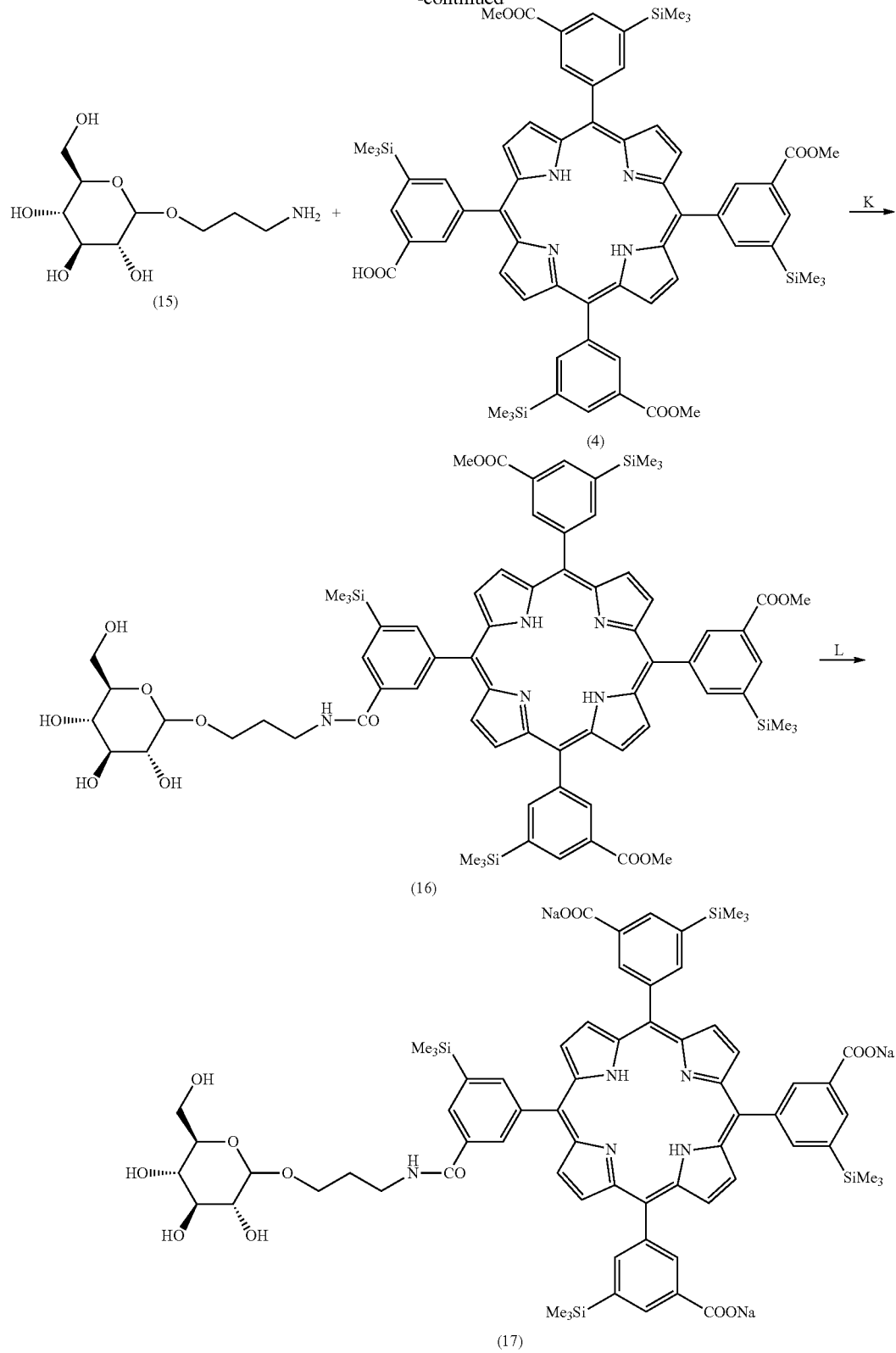

In Pathway H, 3-(tosyl)-n-propyl2,3,4-tri-O-benzyl-α-D-glucopyranoside (Structural Formula (13)) was synthesized. A 200-mL recovery flask was purged with argon, and dry pyridine (5 mL) was added thereto. 3-(n-Octadecyloxy)-n-propyl-2,3-di-O-benzyl-4,6-O-benzylidene-α-D-glucopyranoside (Structural Formula (12)) (0.50 g) and tosyl chloride (0.50 g) were added thereto under stirring, and then the resultant mixture was stirred at room temperature for 2 hours. Next, ethyl acetate (5 mL) was added to the reaction solution, and the resultant mixture was washed with 1 M hydrochloric acid (1 mL) and was then further washed with a saturated aqueous solution of sodium hydrogen carbonate (1 mL). After dried using magnesium sulfate and filtered, the organic phase was concentrated under reduced pressure, and thus a reaction product was obtained. This reaction product was purified through silica gel chromatography (mixed solution of hexane and ethyl acetate), and thus a compound represented by Structural Formula (13) was obtained (0.49 g, 75%).

Figure 22:
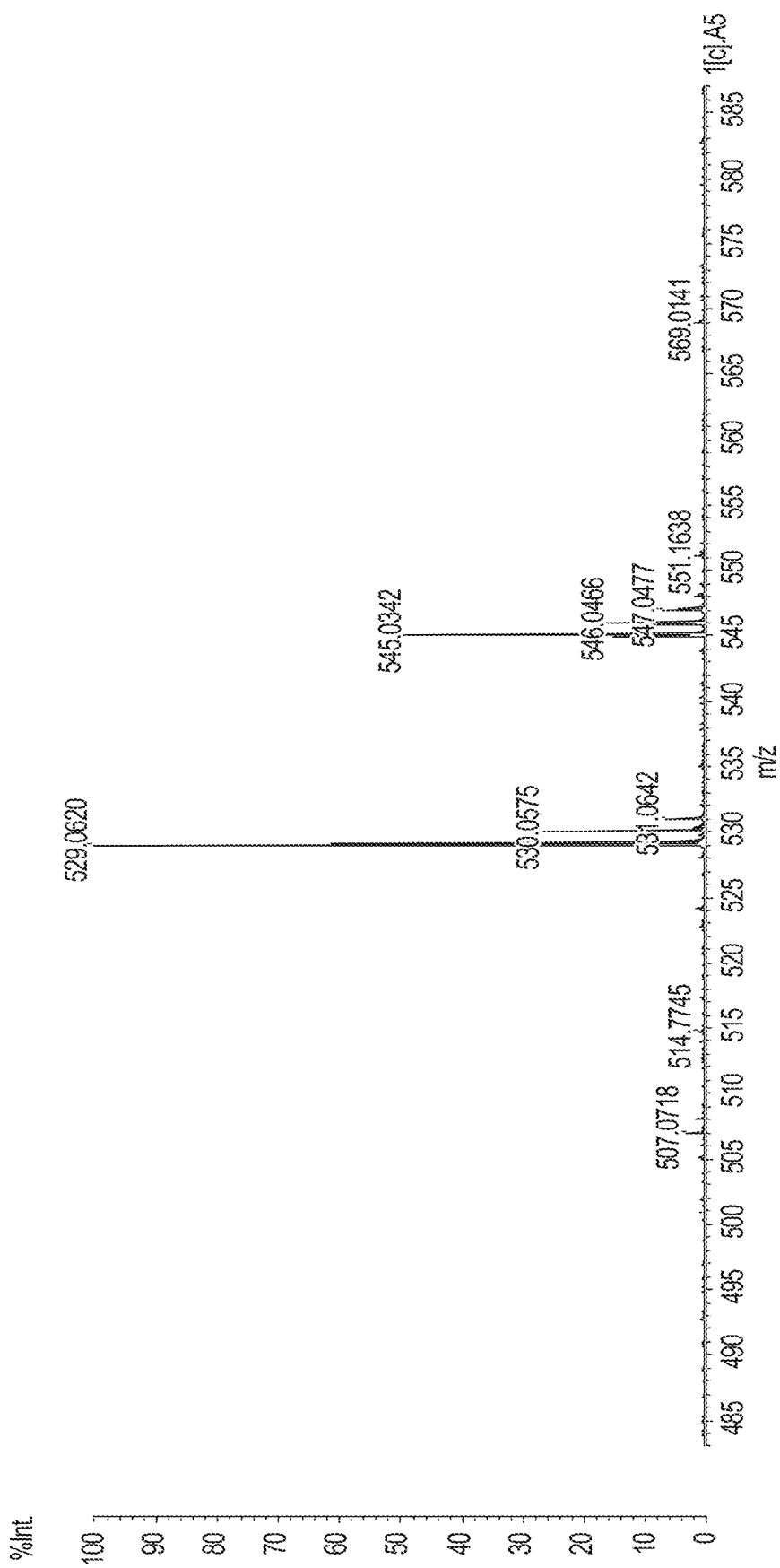
FIG. 22 shows the result of mass spectroscopy of a compound of Structural Formula (12).
Figure 23:
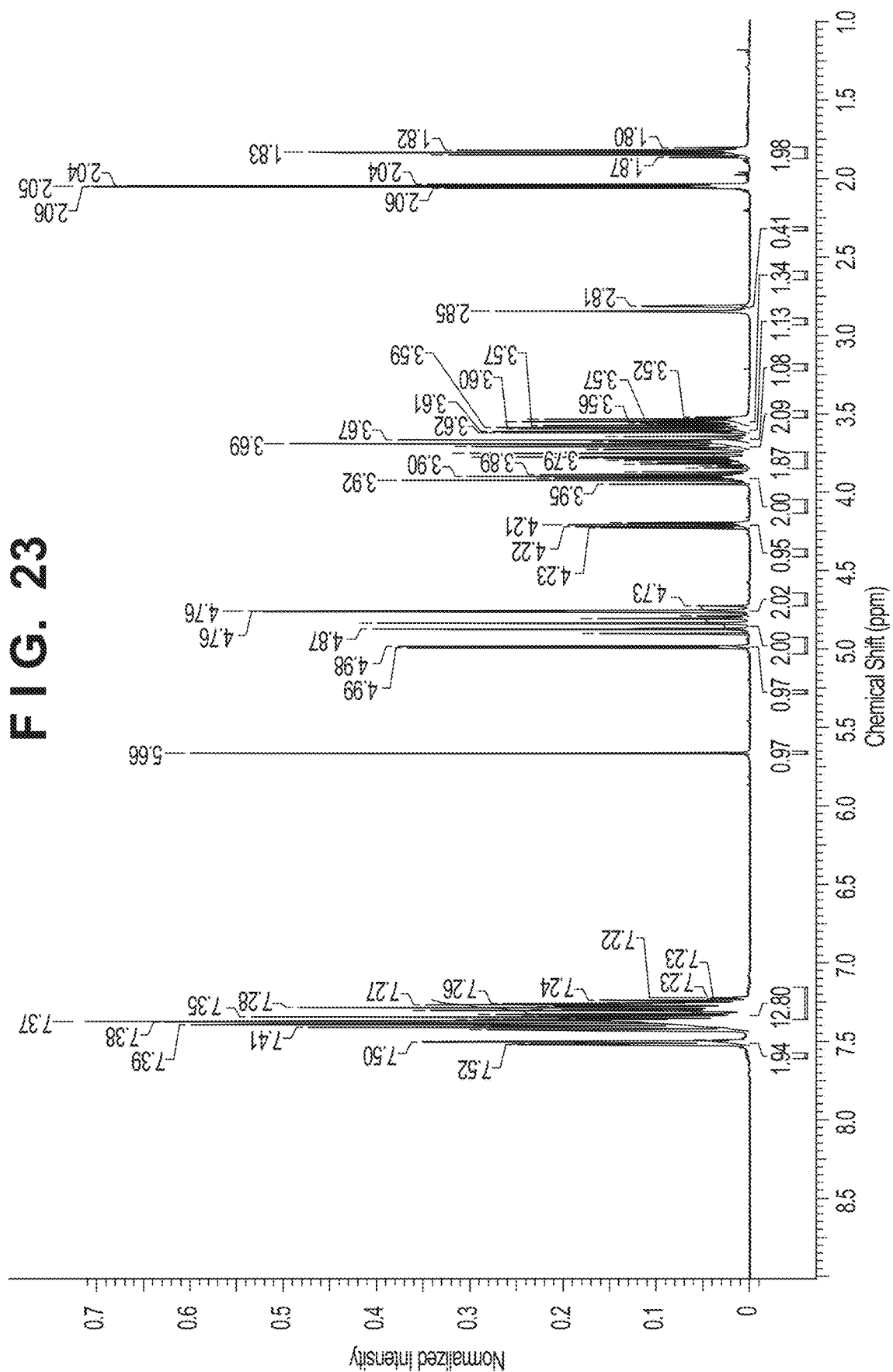
FIG. 23 shows the result of $^1$H-NMR measurement of the compound of Structural Formula (12).
Figure 24:
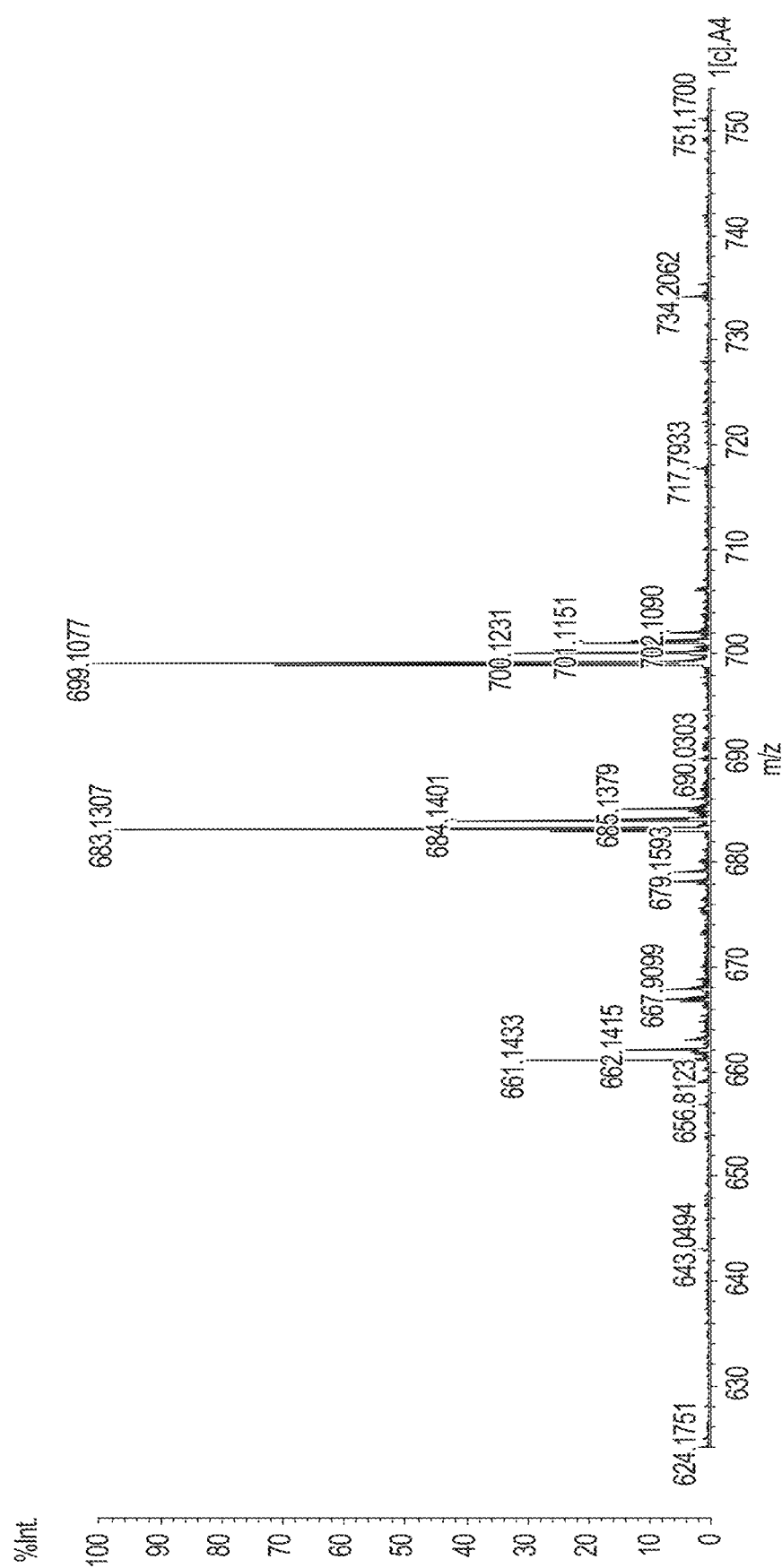
FIG. 24 shows the result of mass spectroscopy of a compound of Structural Formula (13).
Figure 25:
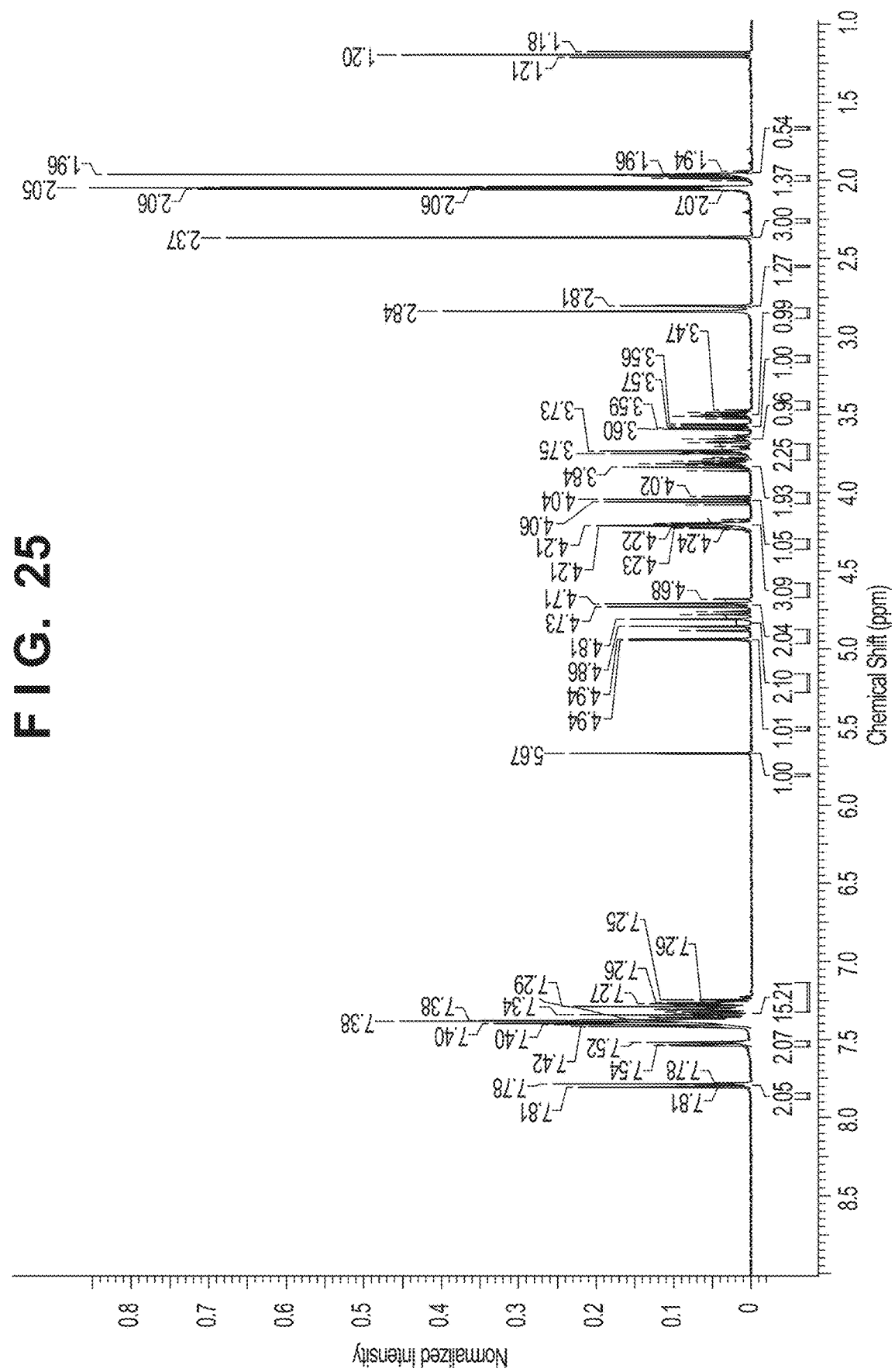
FIG. 25 shows the result of $^1$H-NMR measurement of the compound of Structural Formula (13).

The compound of Structural Formula (12) was subjected to mass spectroscopy and $^1$H-NMR, and the spectra obtained therefrom were shown in FIG. 22 and FIG. 23. Moreover, the compound of Structural Formula (13) was subjected to mass spectroscopy and $^1$H-NMR, and the spectra obtained therefrom were shown in FIG. 24 and FIG. 25.

The following are the data on the spectra obtained through mass spectroscopy and $^1$H-NMR of the compound of Structural Formula (13).

MS: Measured value m/z 661.14 [M+Na], Calculated value 661.24 [M+Na].

δ=7.81-7.78 (m, 2H), 7.54-7.52 (m, 2H), 7.42-7.25 (m, 15H), 5.67 (s, 1H), 4.94 (d, 1H), 4.88-4.78 (q, 2H), 4.76-4.68 (q, 2H), 4.24-4.17 (m, 3H), 4.08-4.02 (q, 1H), 3.86-3.80 (m, 2H), 3.78-3.70 (m, 2H), 3.68-3.63 (m, 1H), 3.60-3.56 (q, 1H), 3.53-3.47 (m, 1H), 2.81 (s, 1H), 2.37 (s, 3H), 2.00-1.97 (t, 1H), 1.96-1.94 (d, 1H) ppm In Pathway I, 3-(azide)-n-propyl-2,3,4-tri-O-benzyl-α-D-glucopyranoside (Structural Formula (14)) was synthesized. A 200-mL recovery flask was purged with argon, and dry dimethylformamide (7 mL) was added thereto. The compound of Structural Formula (13) (0.49 g) and sodium azide (0.50 g) were added thereto under stirring, and the resultant mixture was stirred at 50° C. for 3 hours. Ethyl acetate (5 mL) was added to the reaction solution, and the resultant mixture was washed with a saturated aqueous solution of sodium hydrogen carbonate (5 mL) and was then further washed with saturated saline (5 mL). After dried using magnesium sulfate and filtered, the organic phase was concentrated under reduced pressure, and thus a reaction product was obtained. This reaction product was purified through silica gel chromatography (mixed solution of hexane and ethyl acetate), and thus a compound represented by Structural Formula (14) was obtained (0.36 g, 91%).

Figure 26:
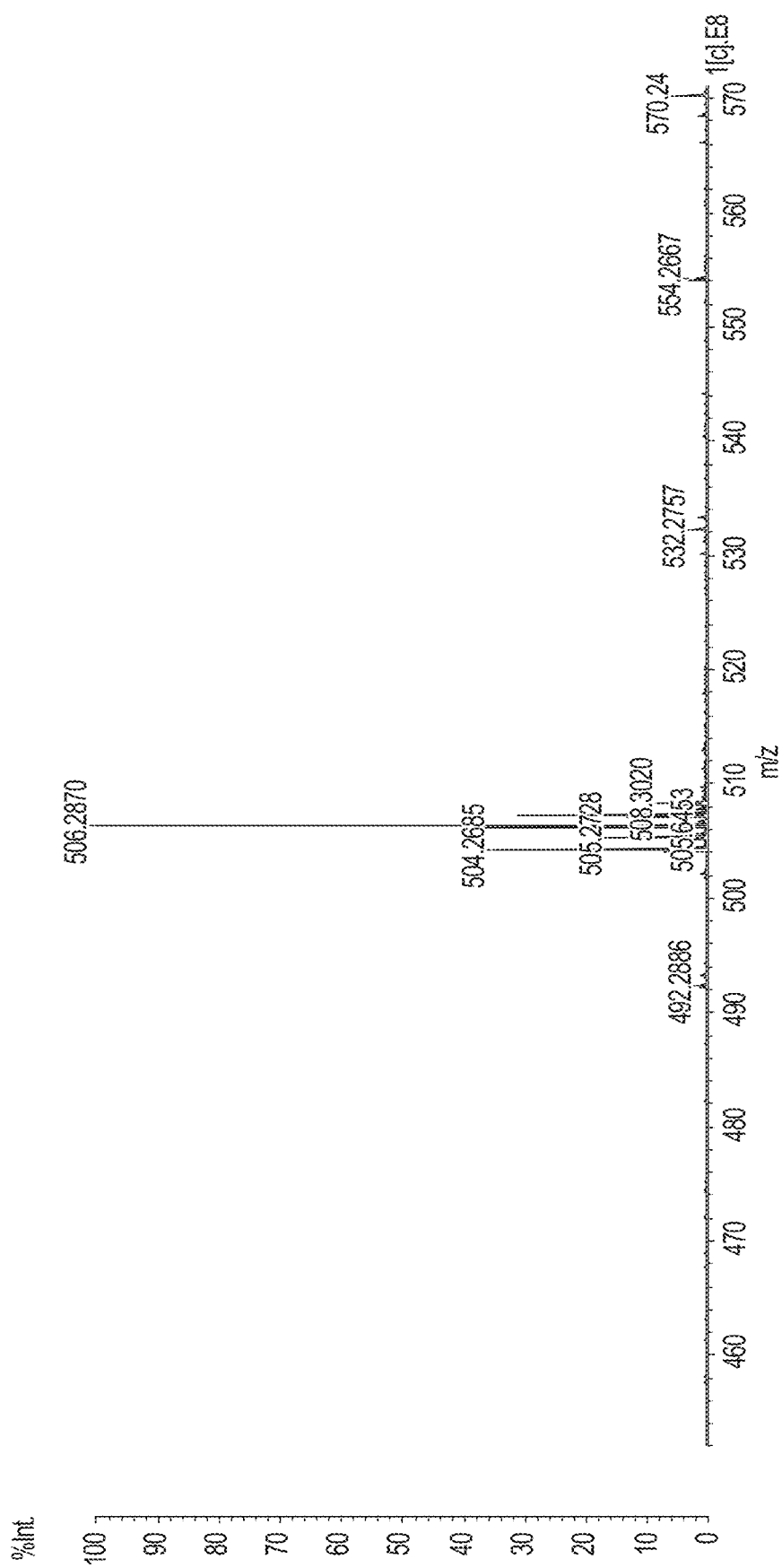
FIG. 26 shows the result of mass spectroscopy of a compound of Structural Formula (14).
Figure 27:
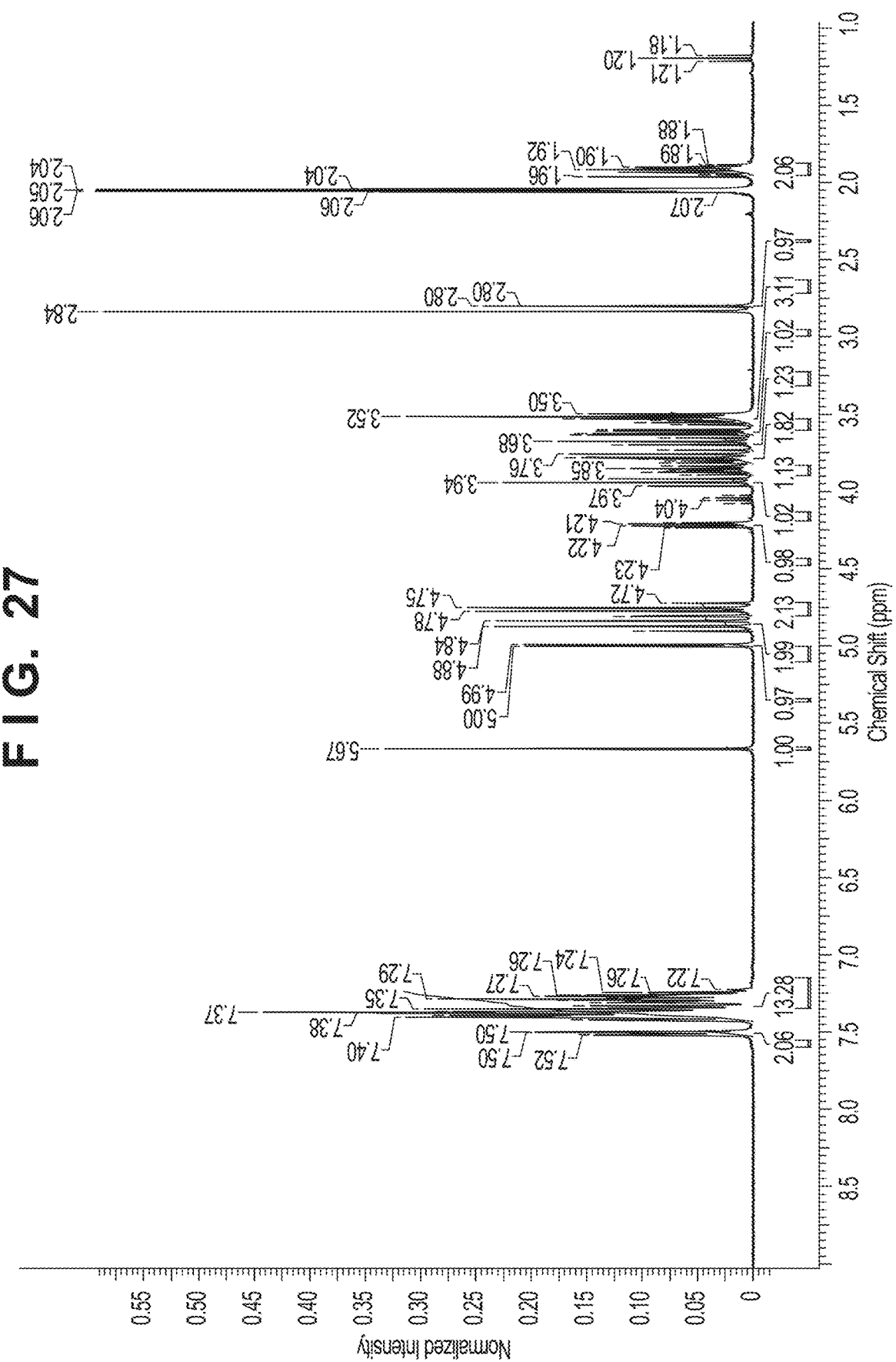
FIG. 27 shows the result of $^1$H-NMR measurement of the compound of Structural Formula (14).

The compound of Structural Formula (14) was subjected to mass spectroscopy and $^1$H-NMR, and the spectra obtained therefrom were shown in FIG. 26 and FIG. 27.

The following are the data on the spectra obtained through mass spectroscopy and $^1$H-NMR of the compound of Structural Formula (14).

MS: Measured value m/z 504.27 [M−N$_2$+H], Calculated value 503.23 [M−N$_2$+H].

δ=7.52-7.49 (m, 2H), 7.43-7.24 (m, 13H), 5.67 (s, 1H), 5.00-4.99 (d, 1H), 4.91-4.81 (q, 2H), 4.81-4.72 (q, 2H), 4.23-4.20 (q, 1H), 3.97-3.92 (t, 1H), 3.89-3.84 (m, 1H), 3.82-3.76 (m, 2H), 3.73-3.65 (q, 1H), 3.63-3.60 (q, 1H), 3.57-3.50 (m, 3H), 2.80 (s, 1H), 1.95-1.88 (m, 2H) ppm In Pathway J, 3-(amino)-n-propyl-α-D-glucopyranoside (Structural Formula (15)) was synthesized. The compound of Structural Formula (14) (0.18 g), palladium hydroxide (0.29 g), tert-butanol (4 mL), and water (4 mL) were added to a 200-mL recovery flask, and the resultant mixture was stirred at 40° C. under a hydrogen atmosphere overnight. This reaction solution was concentrated under reduced pressure, and thus a reaction product was obtained. The reaction product was purified through reversed phase silica gel chromatography (mixed solution of water and methanol), and thus a compound represented by Structural Formula (15) was obtained (30 mg, 37%).

Figure 28:
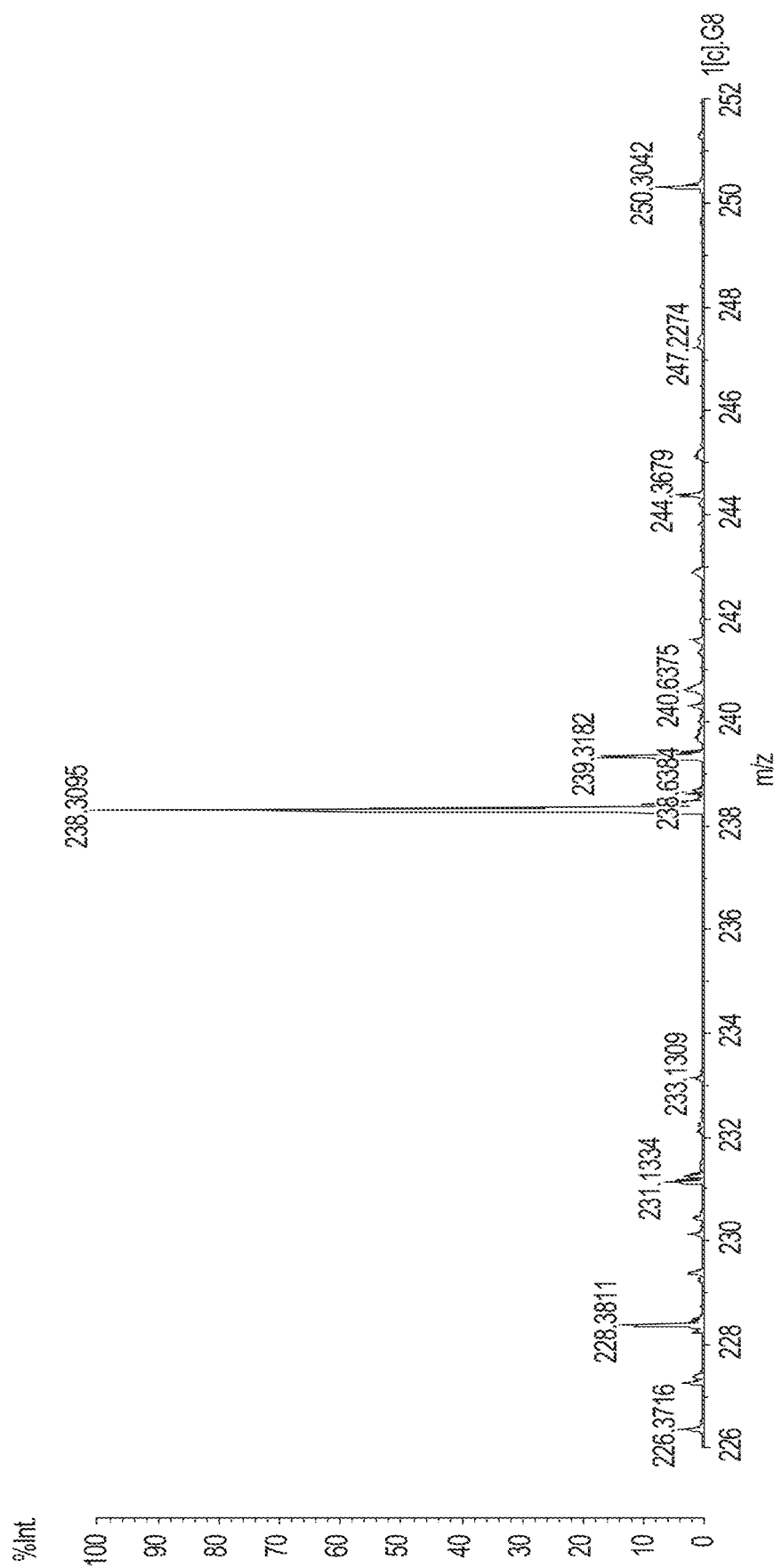
FIG. 28 shows the result of mass spectroscopy of a compound of Structural Formula (15).
Figure 29:
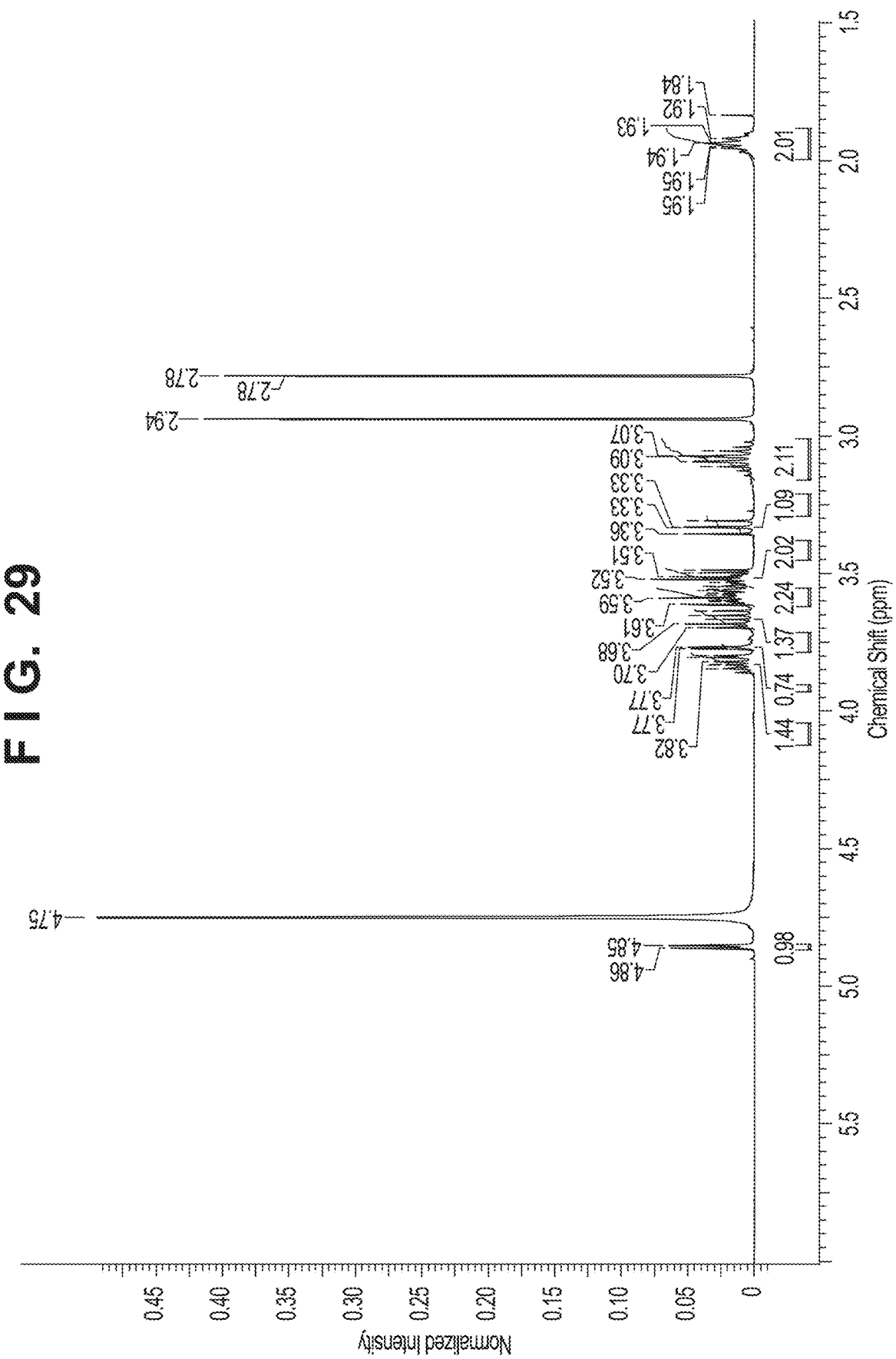
FIG. 29 shows the result of $^1$H-NMR measurement of the compound of Structural Formula (15).

The compound of Structural Formula (15) was subjected to mass spectroscopy and $^1$H-NMR, and the spectra obtained therefrom were shown in FIG. 28 and FIG. 29.

The following are the data on the spectra obtained through mass spectroscopy and $^1$H-NMR of the compound of Structural Formula (15).

MS: Measured value m/z 238.30 [M+H], Calculated value 238.12 [M+H].

δ=4.86-4.85 (d, 1H), 3.86-3.80 (m, 1H), 3.77 (d, 1H), 3.70-3.64 (m, 1H), 3.61-3.55 (m, 2H), 3.55-3.49 (m, 2H), 3.36-3.31 (t, 1H), 3.14-3.02 (m, 2H), 1.97-1.90 (m, 2H) ppm In Pathway K, 3-trimethylsilyl-1-benzenecarboxyamide, N-[3-n-propyl-α-D-glucopyranoside]-5-[10,15,20-tris(3-methoxycarbonyl-5-trimethylsilylphenyl)porphyrin] (Structural Formula (16)) was synthesized. The compound of Structural Formula (4) (10 mg), the compound of Structural Formula (15) (6.3 mg), 1-(3-dimethylaminopropyl)-3-ethyl-carbodiimide hydrochloride (3.5 mg), 1-hydroxybenzotriazole (3.6 mg), diethylaniline (25 μL), and dimethylformamide (1.6 mL) were added to a 50-mL recovery flask. Next, this mixed solution was stirred at room temperature for 13 hours. Ethyl acetate (50 mL) was added to this reaction solution, and the resultant mixture was washed with a saturated aqueous solution of sodium hydrogen carbonate (50 mL) and was then further washed with saturated saline (50 mL). After dried using magnesium sulfate and filtered, the organic phase was concentrated under reduced pressure, and thus a reaction product was obtained. This reaction product was purified through silica gel chromatography (mixed solution of dichloromethane and methanol), and thus a compound represented by Structural Formula (16) was obtained (7.2 mg, 72%).

Figure 30:
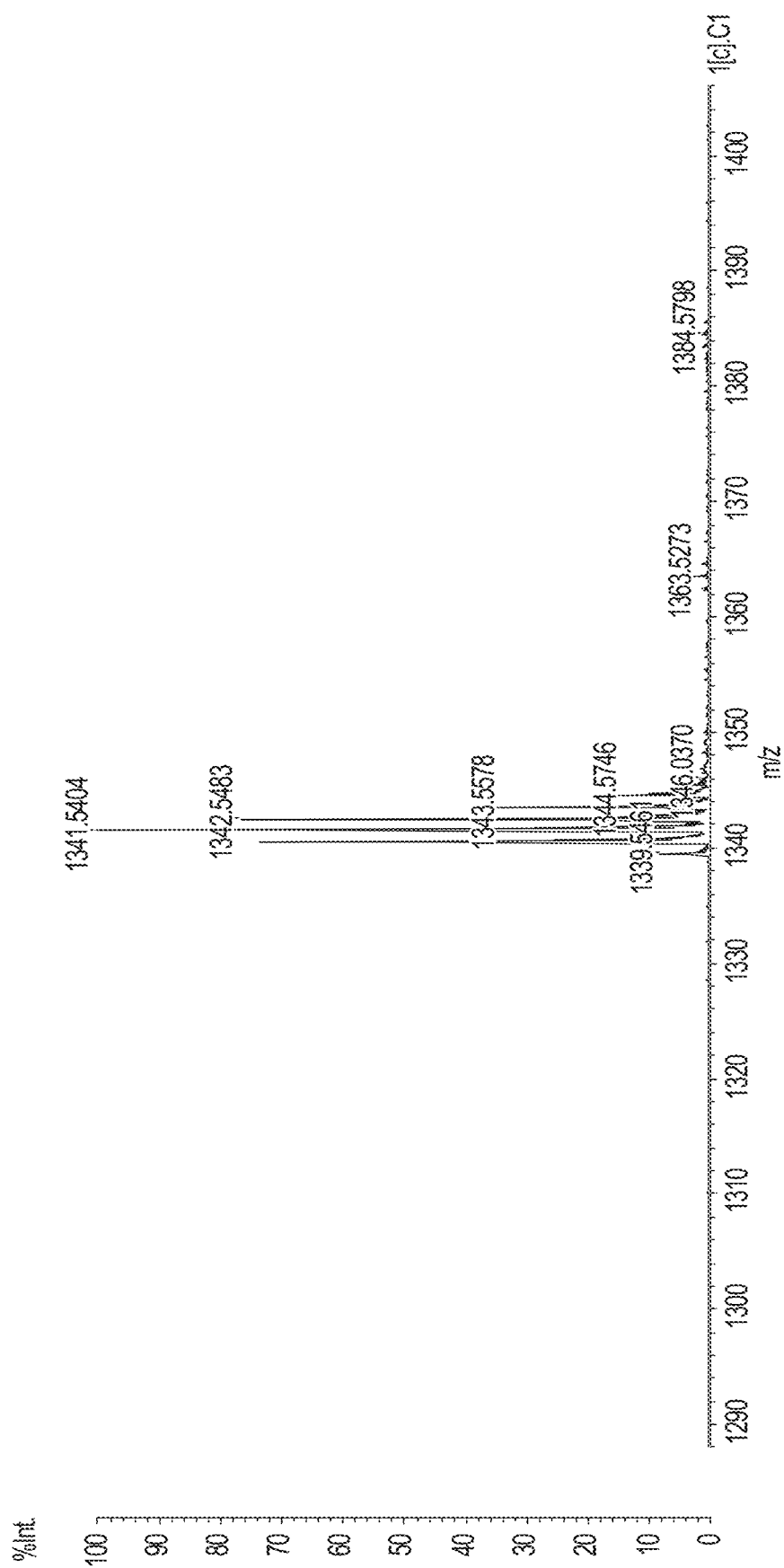
FIG. 30 shows the result of mass spectroscopy of a compound of Structural Formula (16).
Figure 31:
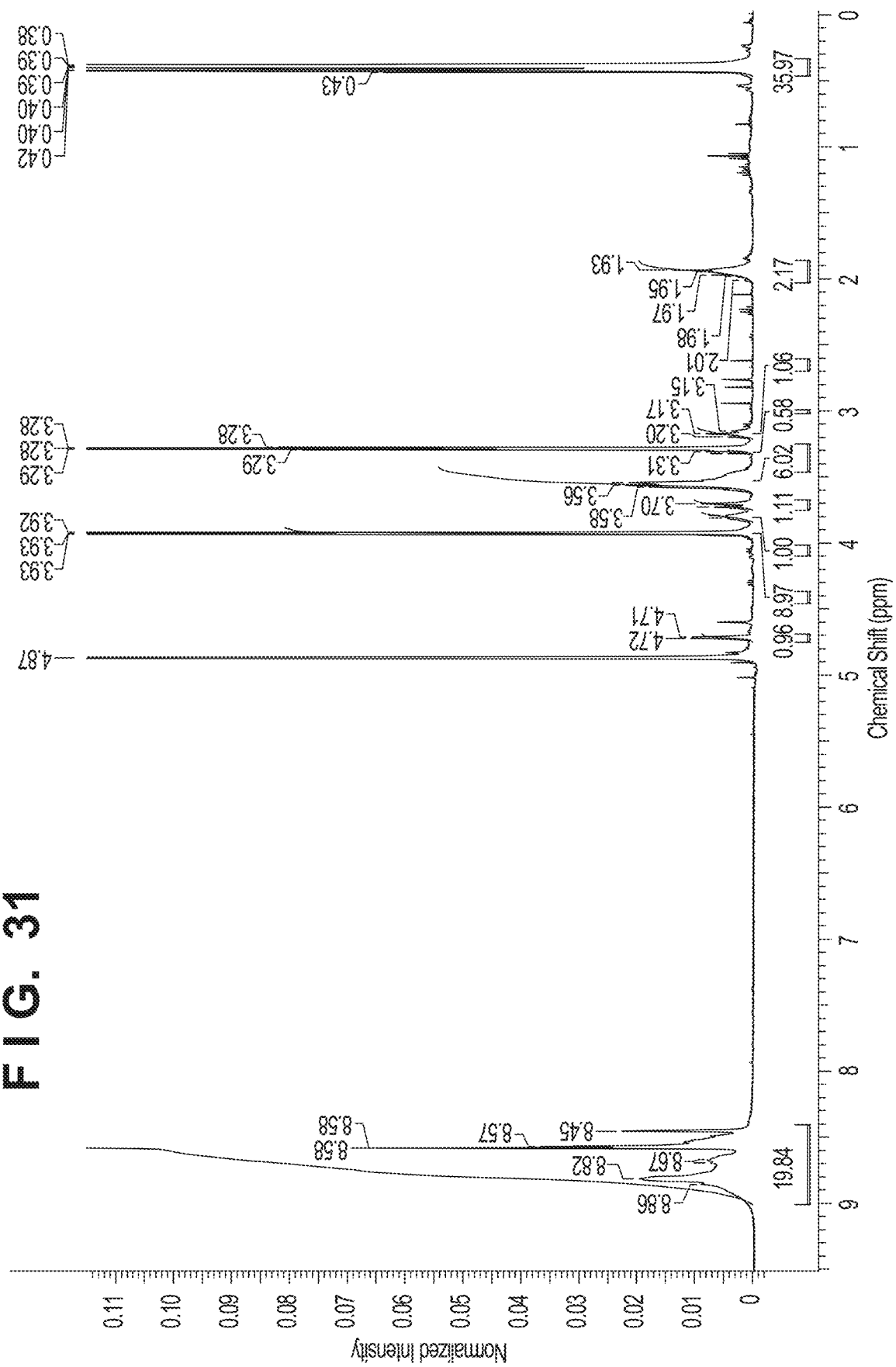
FIG. 31 shows the result of $^1$H-NMR measurement of the compound of Structural Formula (16).

The compound of Structural Formula (16) was subjected to mass spectroscopy and $^1$H-NMR, and the spectra obtained therefrom were shown in FIG. 30 and FIG. 31.

The following are the data on the spectra obtained through mass spectroscopy and $^1$H-NMR of the compound of Structural Formula (16).

MS: Measured value m/z 1341.54 [M+H], Calculated value 1340.52 [M+H].

δ=8.86-8.45 (br, 20H), 4.72-4.71 (m, 1H), 3.92 (s, 9H), 3.81-3.79 (m, 1H), 3.73-3.70 (d, 1H), 3.58-3.54 (m, 6H), 3.32-3.31 (m, 1H), 3.20-3.15 (m, 1H), 2.01-1.93 (m, 2H), 0.43-0.38 (m, 36H) ppm In Pathway L, 3-trimethylsilyl-1-benzenecarboxyamide, N-[3-n-propyl-α-D-glucopyranoside]-5-[10,15,20-tris(3-carbonate-5-trimethylsilylphenyl)porphyrin] trisodium salt (Structural Formula (17)) was synthesized. The compound of Structural Formula (16) (17 mg), a 1 M aqueous solution of sodium hydroxide (150 μL), tetrahydrofuran (2 mL), and methanol (1 mL) were added to a 50-mL recovery flask, and the resultant mixture was stirred at 40° C. for 3 hours. This reaction solution was concentrated under reduced pressure, and thus a reaction product was obtained. The reaction product was purified through reversed phase silica gel chromatography (mixed solution of water and methanol) and was then purified through gel filtration (methanol), and thus a compound represented by Structural Formula (17) was obtained (15.3 mg, 92%). This compound is a sodium salt of a compound represented by Structural Formula (IId) below (also represented by Structural Formula (16)).

[Chemical Formula 9]

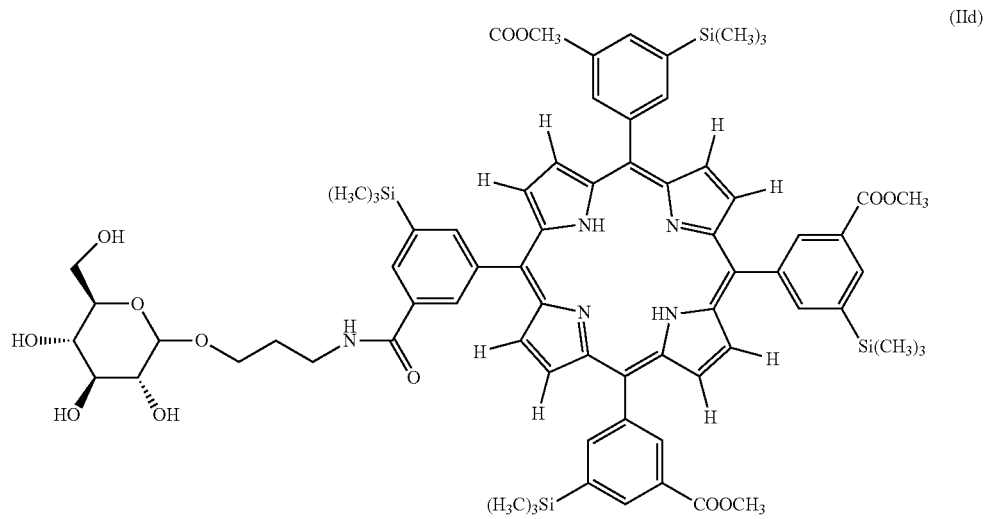

(IId)

Figure 32:
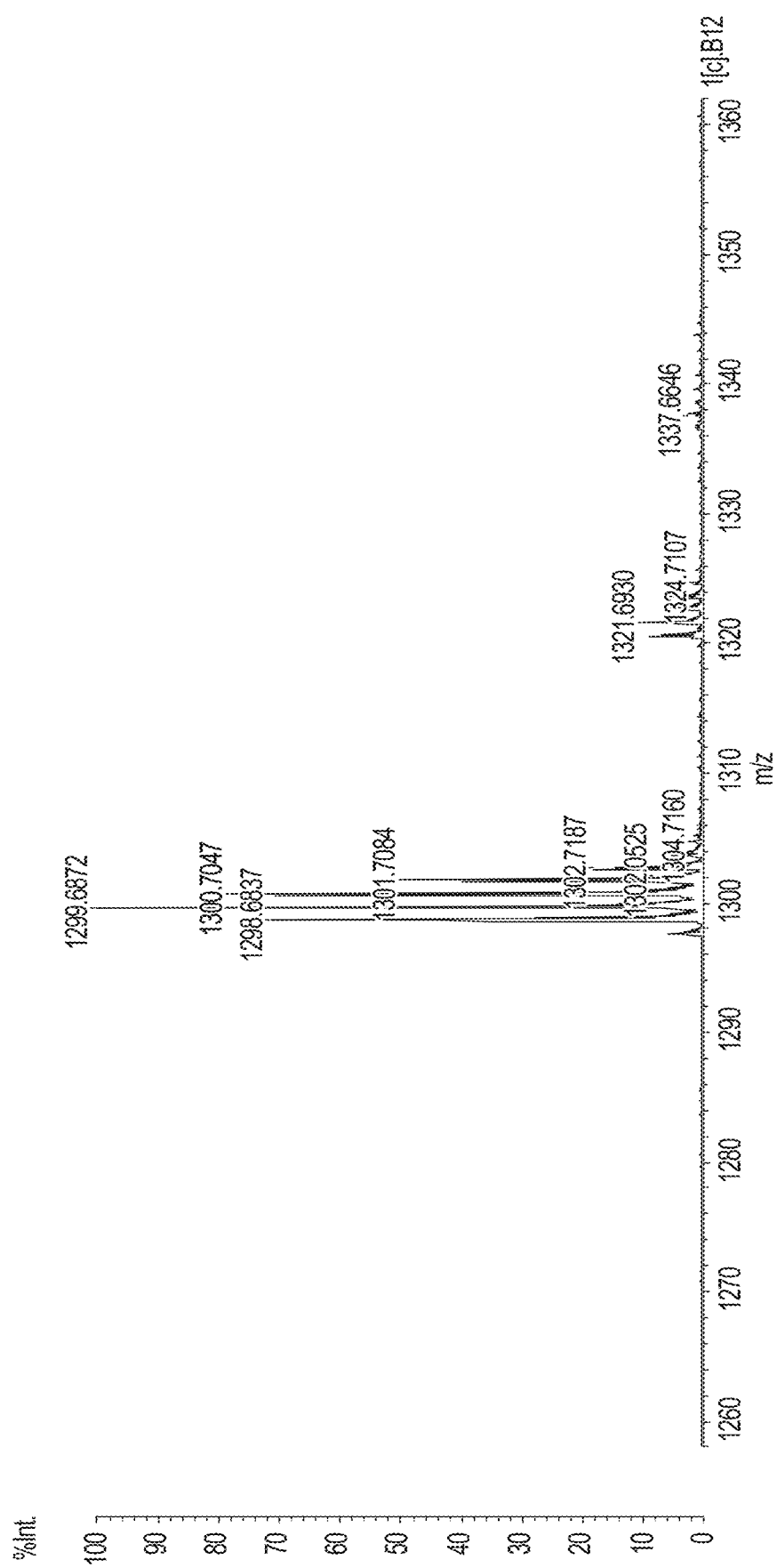
FIG. 32 shows the result of mass spectroscopy of a compound of Structural Formula (17).
Figure 33:
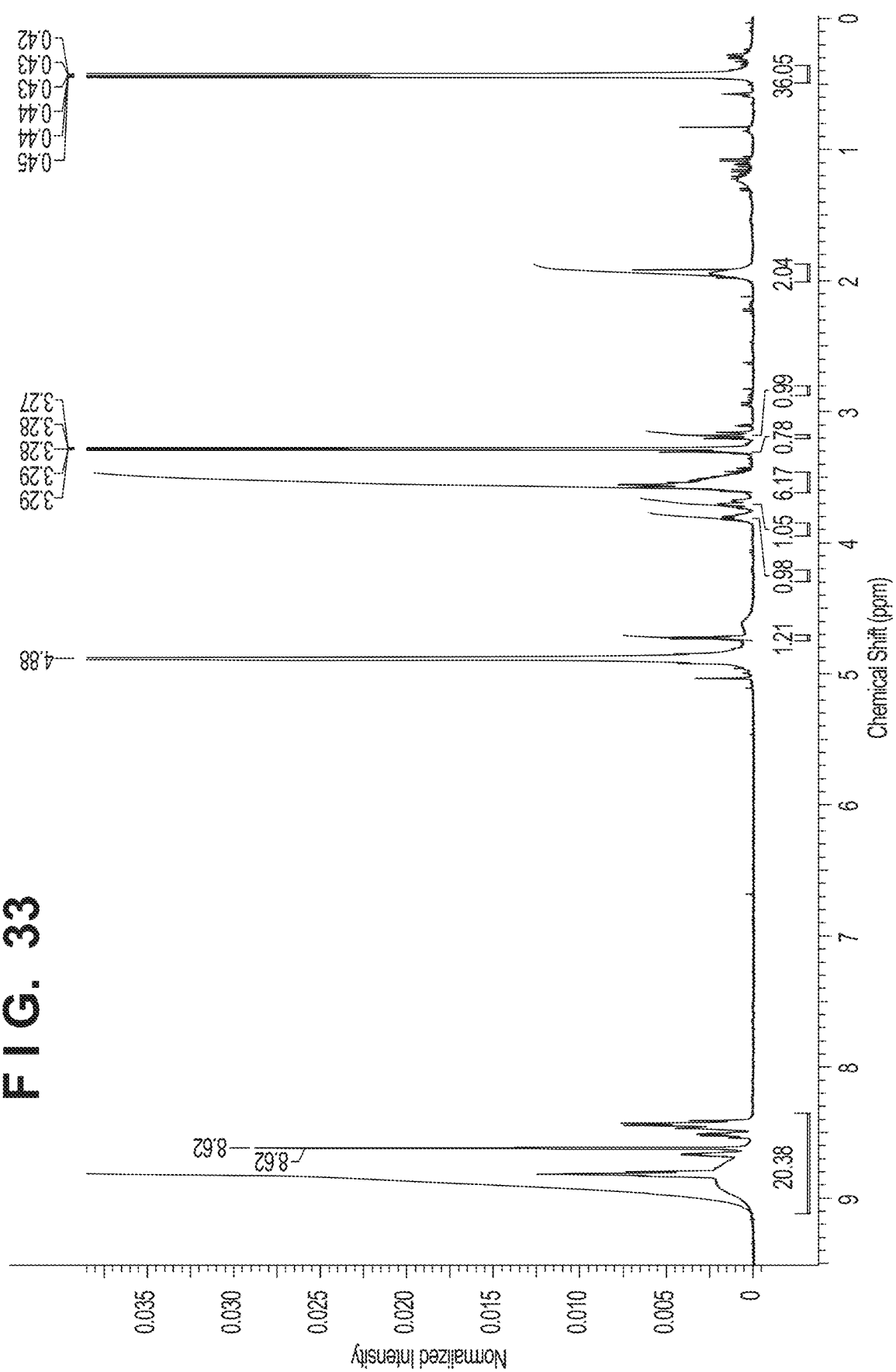
FIG. 33 shows the result of $^1$H-NMR measurement of the compound of Structural Formula (17).

The compound of Structural Formula (17) was subjected to mass spectroscopy and $^1$H-NMR, and the spectra obtained therefrom were shown in FIG. 32 and FIG. 33.

The following are the data on the spectra obtained through mass spectroscopy and $^1$H-NMR of the compound of Structural Formula (17).

MS: Measured value m/z 1298.68 [M–Na$_3$+H$_4$], Calculated value 1298.48 [M–Na$_3$+H$_4$], Mathematical formula C$_{69}$H$_{76}$N$_5$Na$_3$O$_{13}$Si$_4$ δ=8.84-8.41 (br, 20H), 4.74-4.71 (q, 1H), 3.85-3.77 (m, 1H), 3.74-3.67 (m, 1H), 3.60-3.48 (m, 6H), 3.32-3.30 (m, 1H), 3.20-3.16 (t, 1H), 1.94 (br, 2.04), 0.45-0.42 (m, 36H) ppm Example 3

The compounds of Structural Formulae (10) and (11) are formed by introducing a sulfur-containing sugar chain into a compound represented by Structural Formula (III) below, which is a porphyrin analog. As described in Harubumi Kato, "Our Experience With Photodynamic Diagnosis and Photodynamic Therapy for Lung Cancer", Journal of the National Comprehensive Cancer Network, 10 (2012), S-3-8, Hiroaki Horiuchi et al., "Silylation enhancement of photodynamic activity of tetraphenylporphyrin derivative", J. Photochem. Photobiol. A, 2011, 221, 98-104, and Hiroaki Horiuchi, "Silylation Improves the Photodynamic Activity of Tetraphenylporphyrin Derivatives In Vitro and In Vivo", Chem. Eur. J., 2014, 20, 6054-6060, the compound of Structural Formula (III) has excellent optical properties of singlet oxygen. Here, it was confirmed if excellent photochemical properties of the porphyrin compound represented by Structural Formula (III) could be maintained even if a sulfur-containing sugar chain was linked thereto. FIG. 1 collectively shows the absorption spectra and fluorescence spectra of the compounds represented by Structural Formulae (IIa), (IId), and (III). It should be noted that the compounds of Structural Formulae (IIa) and (IId) are obtained by linking a sulfur-containing sugar chain and a sugar chain to the phenyl group of the compound of Structural Formula (III), respectively.

[Chemical Formula 10]

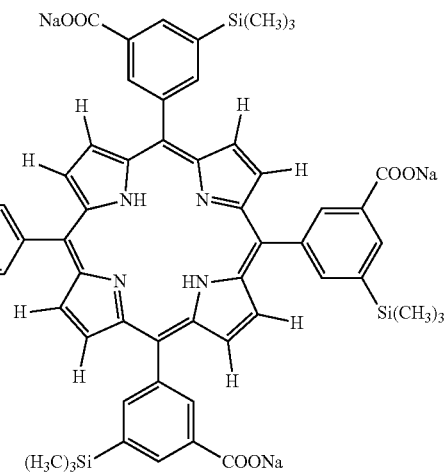

(III)

In the absorption spectrum of the compound of Structural Formula (III), a sharp absorption band called "Soret-band" was observed at 416 nm and an absorption band called "Q-band" was observed near 500 to 650 nm. Moreover, in the absorption spectrum of the compound of Structural Formula (IIa), similar absorption bands were observed.

In the fluorescence spectrum of the compound of Structural Formula (III) excited at 416 nm, peaks were observed at 650 nm and 717 nm, and a similar fluorescence spectrum was also observed in the case of the compound of Structural Formula (IIa). It was shown from these results that the electronic state in the ground state is not different from that in the excited state even when a sulfur-containing sugar chain is linked to the compound of Structural Formula (III).

Next, the fluorescence quantum yields ($\Phi_f$) and fluorescence lifetimes ($\tau_f$) of the compounds were measured. Moreover, the quantum yields ($\Phi_\Delta$) of singlet oxygen generated from the compounds of Structural Formulae (IIa) and (III) were measured. Table 1 shows $\Phi_f$, $\tau_f$, and $\Phi_\Delta$ determined based on the measurement results.

TABLE 1

| Photosensitizing agent | $\Phi_f$ | $\tau_f$ | $\Phi_A$ |
|---|---|---|---|
| IIa | 0.063 | 9.2 | 0.53 |
| IId | 0.056 | 9.3 | — |
| III | 0.054 | 9.0 | 0.57 |

Figure 2:
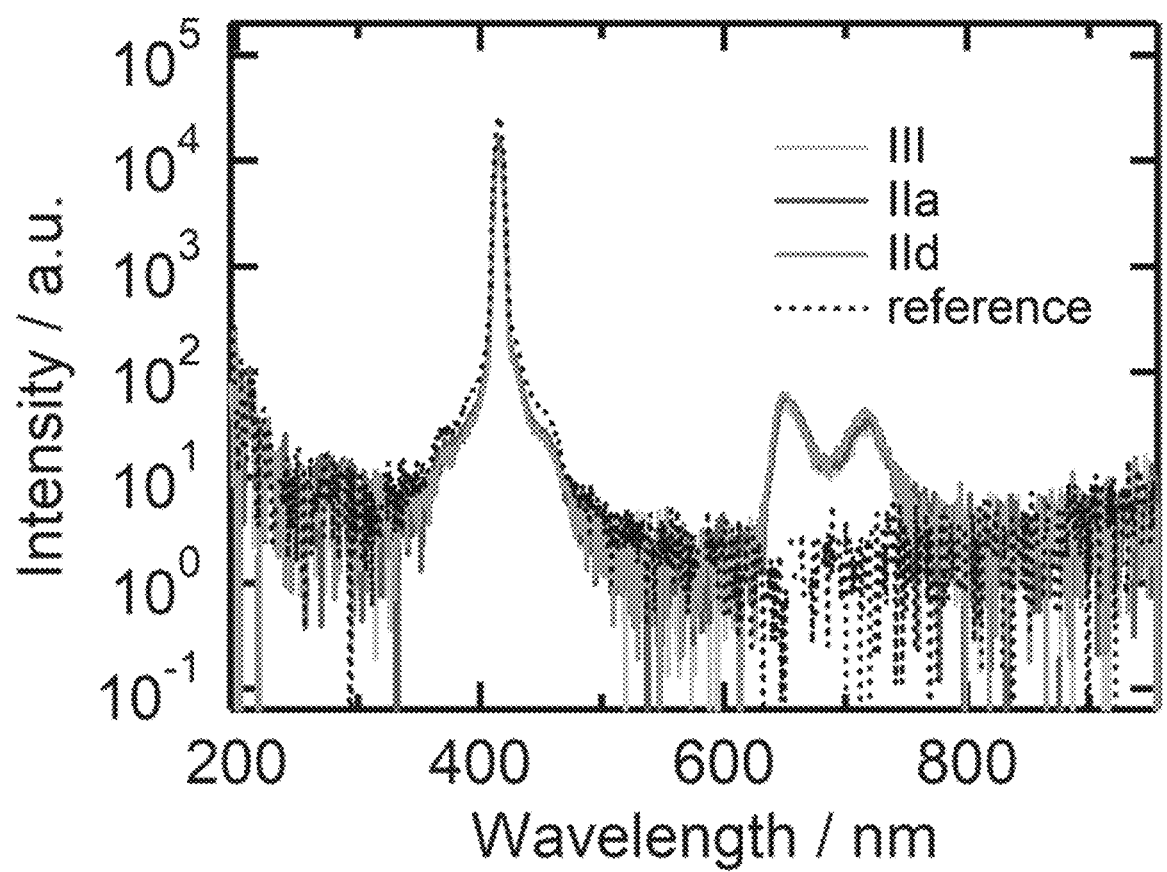
FIG. 2 shows the measurement results of fluorescence quantum yields of the compounds according to Example 3.

FIG. 2 shows spectra obtained by measuring $\Phi_f$ of these compounds using an absolute PL quantum yield spectrometer. It was revealed from these results that the $\Phi_f$ values of the compounds of Structural Formulae (IIa), (IId), and (III) were similar to one another.

Figure 3:
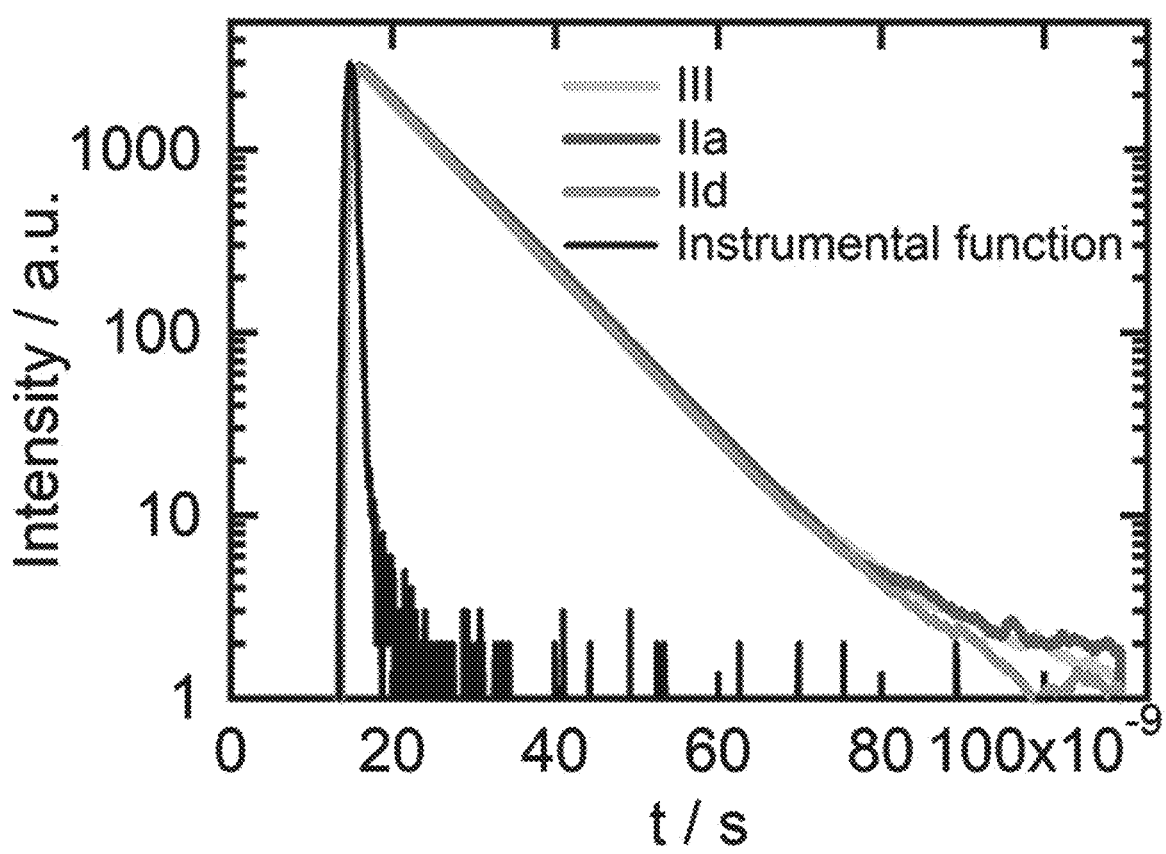
FIG. 3 shows fluorescence decay curves of the compounds according to Example 3.

FIG. 3 shows measurement decay curves based on the measurement results of $\tau_f$ from the compounds. Each of the fluorescence decay curves was subjected to curve fitting with a monoexponential function using a deconvolution method, and thus $\tau_f$ was determined. It was revealed from these results that the $\tau_f$ values of the compounds of Structural Formulae (IIa), (IId), and (III) were similar to one another.

Figure 4:
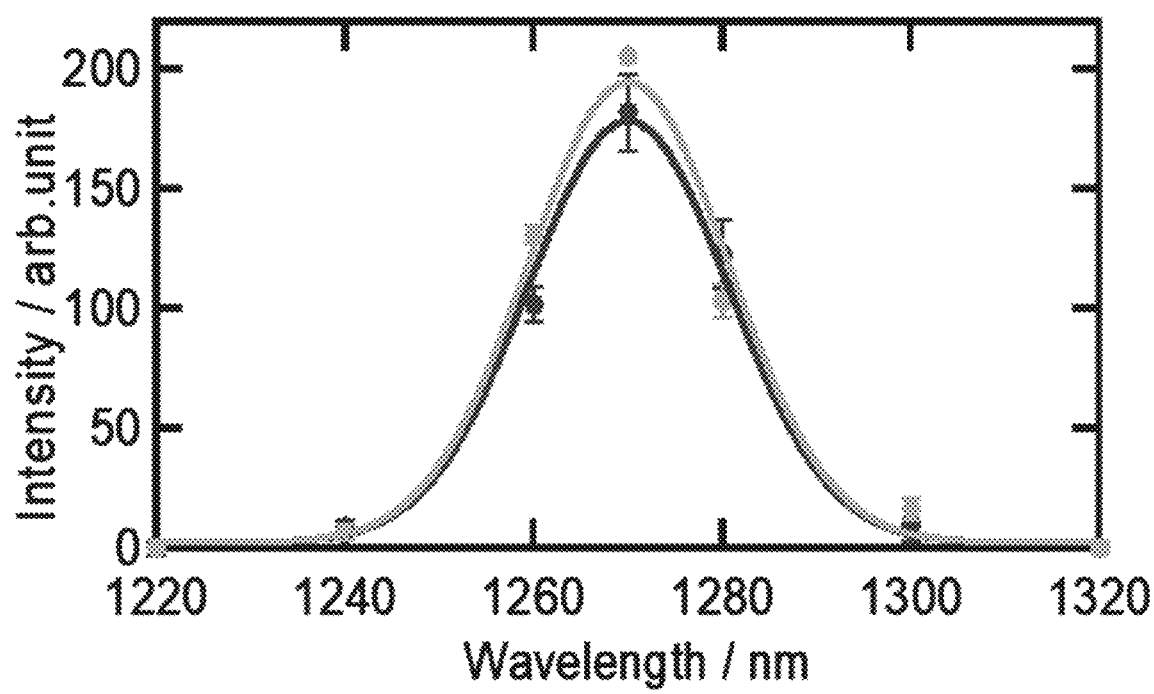
FIG. 4 shows phosphorescence spectra of the photoexcited compounds according to Example 3.

Next, the measurement of $\Phi_A$ will be described. First, the compounds of Structural Formula (IIa) and (III) were each dissolved in ethanol at such a concentration that gave an absorbance of 0.1, and then were irradiated with light at 355 nm using $Nd^{3+}$:YAG LASER (LS-2137U, manufactured by Lotis TII). Next, singlet oxygen was measured using a self-produced infrared emission measurement apparatus in which a near-infrared photomultiplier tube (R5509-42, manufactured by Hamamatsu Photonics K.K.) is used. It should be noted that singlet oxygen was measured 17 times, and the average value was shown as a phosphorescence spectrum in FIG. 4. Singlet oxygen emits phosphorescence at a near-infrared wavelength 1270 nm. Therefore, in this specification, $\Phi_A$ was determined by measuring the intensity of such phosphorescence. TPPS ($\Phi_A$=0.63) was used as a standard substance for determination of $\Phi_A$. $\Phi_A$ of the compound of Structural Formula (IIa) and $\Phi_A$ of the compound of Structural Formula (III) were determined as 0.57 and 0.53, respectively. It can be considered from these results that the quantum yield of singlet oxygen generated from the compound of Structural Formula (IIa) was as high as that from the compound of Structural Formula (III).

Example 4

The compound of Structural Formula (III) to which a sulfur-containing sugar-chain is linked is more likely to accumulate in tumor. Regarding such an improvement in the accumulation, the following describes the evaluation of the efficiency of uptake of the compounds of structural Formulae (IIa) and (III) by cancer cells.

Human-derived A549 cells were used as cancer cells. Dulbecco's Modified Eagle Medium (DMEM) supplemented with 10% Fetal Bovine Serum (FBS: manufactured by EQUITECH-BIO, INC.) and 1% Penicillin Streptomycin Glutamine (Invitrogen (trademark)) was used as a culture medium, which will be described later. Phosphate buffered saline (PBS) was used as a cell washing solution, and PBS containing 0.05% trypsin and 0.02% EDTA was used as a cell detaching solution. A circular plastic petri dish (Greiner Bio-one, 628160) with a diameter of 6 cm was used as a culture container.

First, an A549 cell suspension was cultured on a culture medium. 100 μL of the cell suspension was added to each well of a black 96-well plate and cultured at 37° C. in a 5% $CO_2$ atmosphere for a day. Thereafter, the cells were washed with PBS, 100 μL of a solution obtained by adding 10% FBS, 10% BSA (Cohn Fraction V, pH=7.0, manufactured by Wako Pure Chemical Industries, Ltd.), and the individual photosensitizing agent at a final concentration of 3 μM to DMEM was added to each well, and then the cells were incubated for 12 hours. Next, the cells were washed twice with DMEM containing 10% FBS and then washed twice with Fluoro Brite (trademark) DMEM to remove the extracellular photosensitizing agent. Furthermore, the concentrations of the photosensitizing agents inside the cells were quantified using a fluorescence micro plate reader (Infinite M200 Pro, manufactured by TECAN). For the fluorescence observation, the excitation wavelength was 418 nm, and the observation wavelength was 646 nm.

Figure 5:
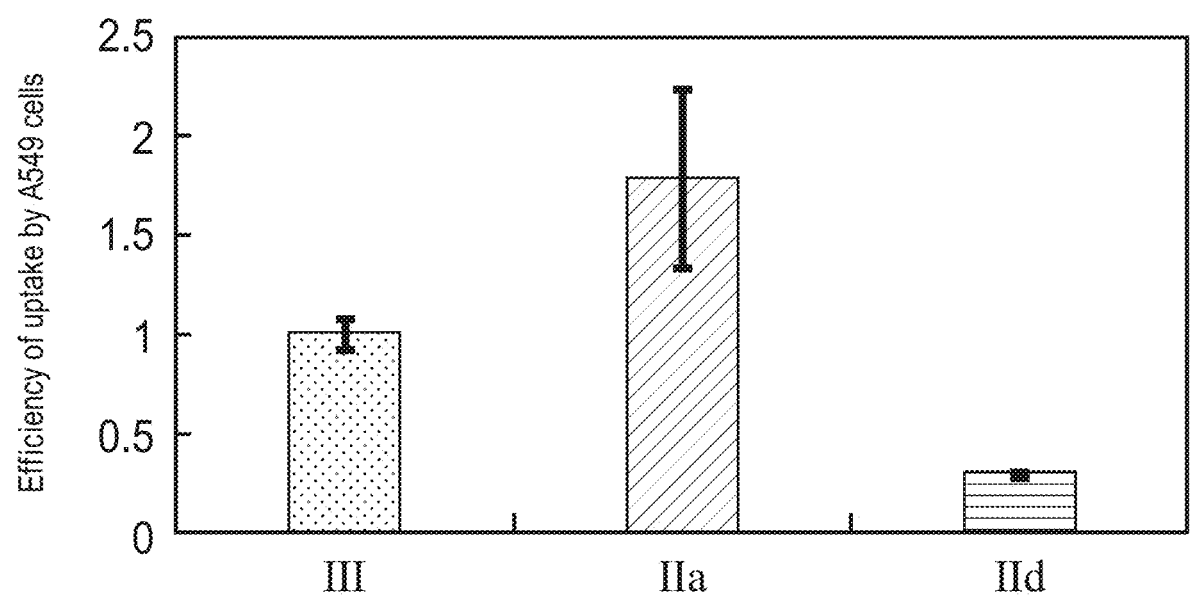
FIG. 5 shows the efficiency of uptake of the compounds according to Example 4 by cancer cells.

FIG. 5 shows the measurement results of relative uptake efficiency based on the uptake efficiency in the case where the compound of Structural Formula (III) was added. The uptake efficiency in the case where the compound of Structural Formula (IIa) was added was 1.8 times as high as that in the case where the compound of Structural Formula (III) was added. It can be concluded from these results that the efficiency of uptake by cancer cells was improved by introducing a sulfur-containing sugar chain. On the other hand, uptake by cancer cells also occurred even in the case where a sugar chain contained no sulfur atoms (e.g., $R_{13}$=OH), and it was thus found that use as a sensitizing agent and a fluorescent probe was possible.

Accordingly, it is revealed that introducing a sugar chain together with a silicon substituent into a photosensitizing agent makes it possible to obtain a compound that accumulates selectively in a tumor tissue and then efficiently generates singlet oxygen and that emits fluorescence and is thus favorably used to treat and diagnose cancers and the like. It is expected that a PDT treatment effect is improved by using such a photosensitizing agent.

The invention is not limited to the foregoing embodiments, and various variations/changes are possible within the spirit of the invention.

What is claimed is:

1. A compound represented by Formula (I) below or a salt thereof;

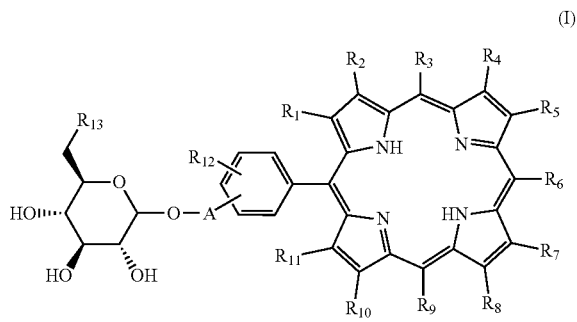

(I)

where A is a linking group represented as —X—NHCO— where X is a $C_1$ to $C_6$ alkylene group, each of $R_1$, $R_2$, $R_4$, $R_5$, $R_7$, $R_8$, $R_{10}$, and $R_{11}$ is a hydrogen atom, each of $R_3$, $R_6$, and $R_9$ is a substituent of Formulae (iii) below;

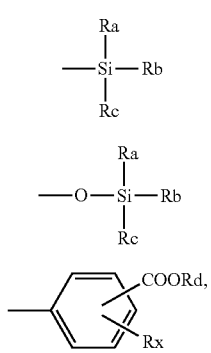

$R_{12}$ is selected from a group of substituents represented by Formula (i) or (ii) above,
$R_{13}$ is a sulfo group,
Ra, Rb, and Rc in Formula (i) and (ii) above are substituents independently selected from $C_1$ to $C_6$ alkyl groups, and
Rd in Formula (iii) above is a hydrogen atom or a $C_1$ to $C_6$ alkyl group, and Rx in Formula (iii) above is a substituent represented by General Formula (i) or (ii) above.

2. The compound or the salt thereof according to claim 1, wherein Ra, Rb, and Rc in Formulae (i) and (ii) above each are a methyl group.

3. The compound or the salt thereof according to claim 1, wherein Rd in Formula (iii) above is a methyl group.

4. The compound or the salt thereof according to claim 1, wherein R12 is a trialkylsilyl group.

5. The compound or the salt thereof according to claim 1, wherein the substituents $R_{12}$ and A link to meta positions relative to a porphyrin ring-linking site.

6. A compound represented by Formula (IIb) below or a salt thereof;

7. A method of treating a patient suffering from cancer, comprising administering, to the patient, an effective amount of a compound or the salt thereof, wherein the compound is represented by Formula (I) below or a salt thereof;

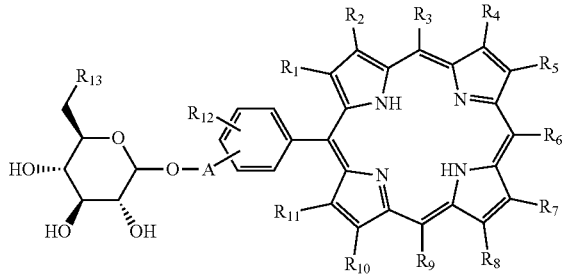

where A is a linking group represented as —X—NHCO— where X is a $C_1$ to $C_6$ alkylene group, each of $R_1$, $R_2$, $R_4$, $R_5$, $R_7$, $R_8$, $R_{10}$, and $R_{11}$ is a hydrogen atom, each of $R_3$, $R_6$, and $R_9$ is a substituent of Formulae (iii) below;

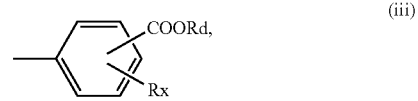

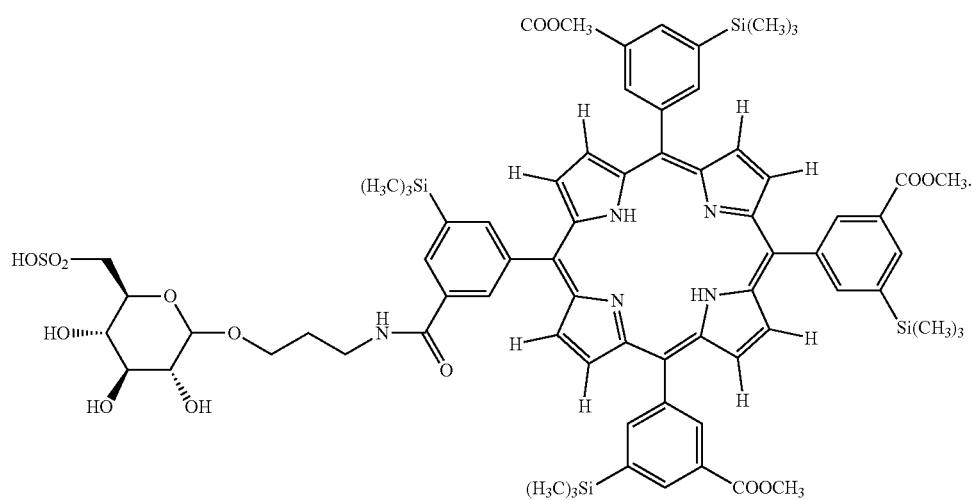

$R_{12}$ is selected from a group of substituents represented by Formula (i) or (ii) above, $R_{13}$ is a sulfo group, Ra, Rb, and Rc in Formula (i) and (ii) above are substituents independently selected from $C_1$ to $C_6$ alkyl groups, and Rd in Formula (iii) above is a hydrogen atom or a $C_1$ to $C_6$ alkyl group, and Rx in Formula (iii) above is a substituent represented by General Formula (i) or (ii) above.

8. A method comprising administering a photosensitizing agent for photodynamic therapy containing a compound or the salt thereof, wherein the compound is represented by Formula (I) below or a salt thereof;

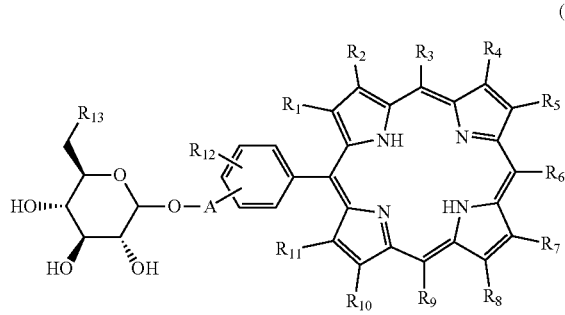
(I)

where A is a linking group represented as —X—NHCO— where X is a $C_1$ to $C_6$ alkylene group, each of $R_1$, $R_2$, $R_4$, $R_5$, $R_7$, $R_8$, $R_{10}$, and $R_{11}$ is a hydrogen atom, each of $R_3$, $R_6$, and $R_9$ is a substituent of Formulae (iii) below;

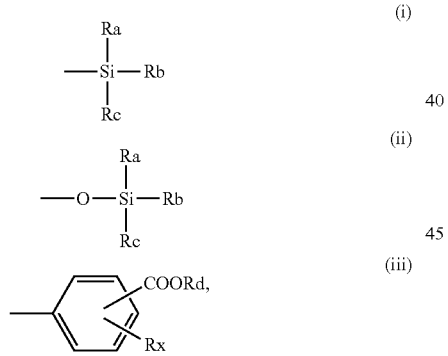

$R_{12}$ is selected from a group of substituents represented by Formula (i) or (ii) above, $R_{13}$ is a sulfo group, Ra, Rb, and Rc in Formula (i) and (ii) above are substituents independently selected from $C_1$ to $C_6$ alkyl groups, and Rd in Formula (iii) above is a hydrogen atom or a $C_1$ to $C_6$ alkyl group, and Rx in Formula (iii) above is a substituent represented by General Formula (i) or (ii) above.

9. A method comprising administering a fluorescent probe composition containing a compound or the salt thereof, wherein the compound is represented by Formula (I) below or a salt thereof;

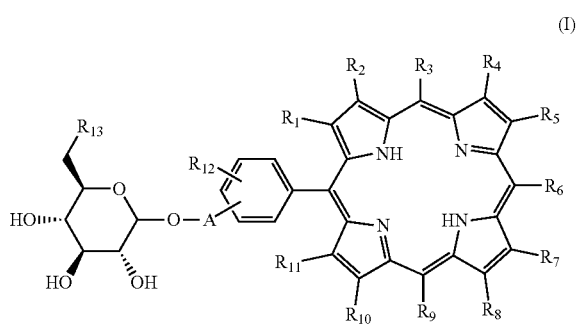
(I)

where A is a linking group represented as —X—NHCO— where X is a $C_1$ to $C_6$ alkylene group, each of $R_1$, $R_2$, $R_4$, $R_5$, $R_7$, $R_8$, $R_{10}$, and $R_{11}$ is a hydrogen atom, each of $R_3$, $R_6$, and $R_9$ is a substituent of Formulae (iii) below;

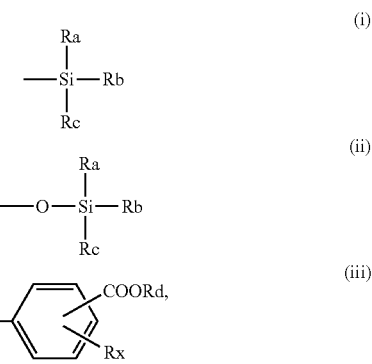

$R_{12}$ is selected from a group of substituents represented by Formula (i) or (ii) above, $R_{13}$ is a sulfo group, Ra, Rb, and Rc in Formula (i) and (ii) above are substituents independently selected from $C_1$ to $C_6$ alkyl groups, and Rd in Formula (iii) above is a hydrogen atom or a $C_1$ to $C_6$ alkyl group, and Rx in Formula (iii) above is a substituent represented by General Formula (i) or (ii) above.

* * * * *